(12) United States Patent
Olsen et al.

(10) Patent No.: US 8,428,967 B2
(45) Date of Patent: Apr. 23, 2013

(54) SPOT CHECK MONITOR CREDIT SYSTEM

(75) Inventors: Gregory A. Olsen, Trabuco Canyon, CA (US); Marcelo Lamego, Coto De Caza, CA (US); Cristiano Dalvi, Irvine, CA (US); Johannes Bruinsma, Mission Viejo, CA (US); Jeroen Poeze, Mission Viejo, CA (US); Massi Joe E. Kiani, Laguna Niguel, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 15 days.

(21) Appl. No.: 13/110,833

(22) Filed: May 18, 2011

(65) Prior Publication Data

US 2011/0218816 A1  Sep. 8, 2011

Related U.S. Application Data

(63) Continuation of application No. 12/882,111, filed on Sep. 14, 2010.

(60) Provisional application No. 61/242,384, filed on Sep. 14, 2009, provisional application No. 61/242,792, filed on Sep. 15, 2009, provisional application No. 61/352,361, filed on Jun. 7, 2010, provisional application No. 61/354,251, filed on Jun. 13, 2010, provisional application No. 61/382,812, filed on Sep. 14, 2010, provisional application No. 61/352,345, filed on Jun. 7, 2010.

(51) Int. Cl.
   *G06Q 50/00* (2012.01)
(52) U.S. Cl.
   USPC .......................................................... 705/2

(58) Field of Classification Search ....... 705/2; 600/300
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |

(Continued)

OTHER PUBLICATIONS

Partial International Search Report for PCT Application No. PCT/US2010/048825, mailed on Feb. 20, 2012 in 7 pages.

*Primary Examiner* — John Pauls
(74) *Attorney, Agent, or Firm* — Knobbe Martens Olson & Bear LLP

(57) ABSTRACT

A spot check credit system advantageously includes various embodiments for obtaining authorization or payment for each measurement, groups of measurements, times of measurement or the like. In an embodiment, the system utilizes a server that communicates web pages over a computer network. In an embodiment, the system utilizes a digital communication device such as a photocommunicative key.

12 Claims, 35 Drawing Sheets

U.S. PATENT DOCUMENTS

| | | | |
|---|---|---|---|
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,631,353 B1 | 10/2003 | Davis et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |

| Patent | Date | Inventor |
|---|---|---|
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 2002/0120467 A1 | 8/2002 | Buanes |
| 2009/0076844 A1 | 3/2009 | Koegen |

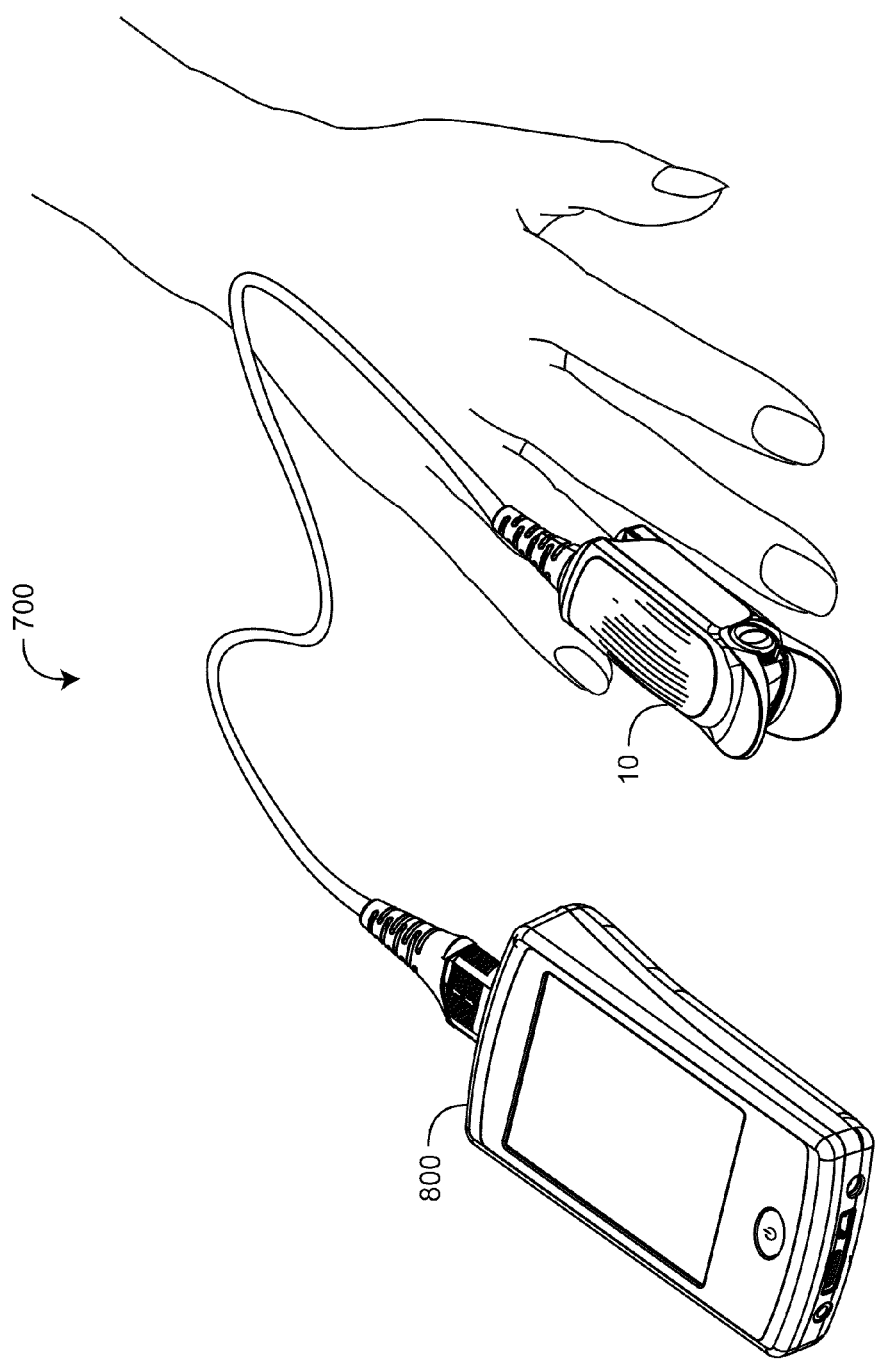

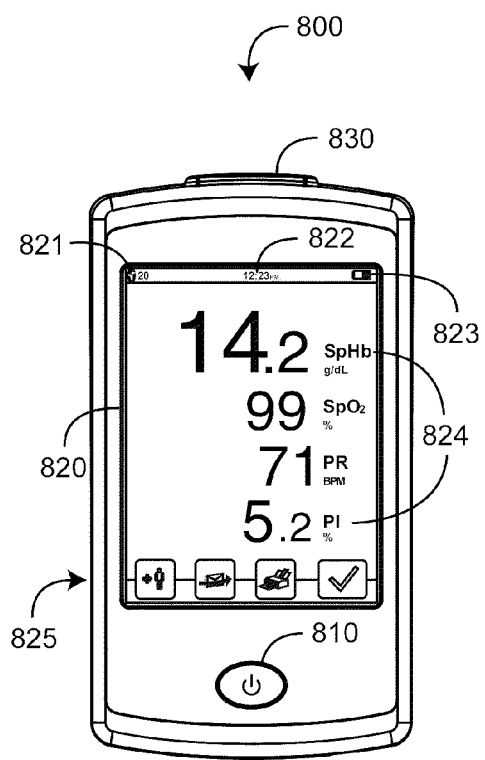
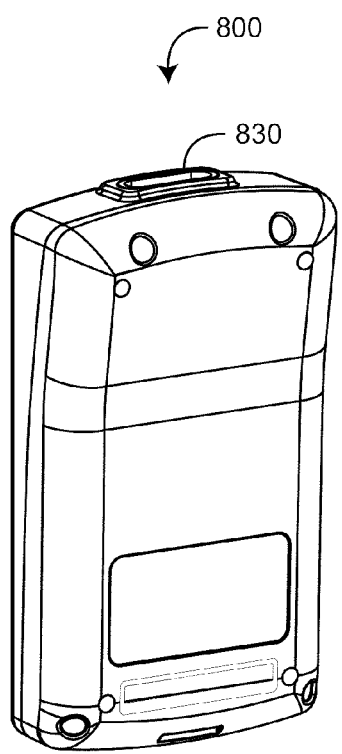
FIG. 8A  FIG. 8B
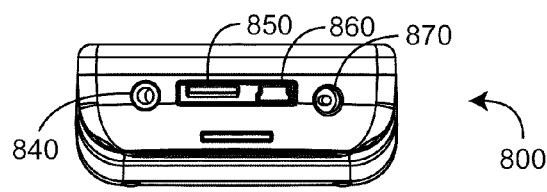
FIG. 8C

FIG. 15A

[ Create New Customer Account ] [ My Customers ] [ Issue Credits ] [ Notify All Customers ]

Issue Spot Check Credits

| | |
|---|---:|
| Total Customer Count | 27 |
| Total Monitors | 35 |
| Total Sensors | 38 |
| Total Spot Check Credits | 200,000 |

| Customer | Sensor Usage | Issue Spot Checks |
|---|---:|---:|
| Irvine Walkin Clinic/Dr. A. Jones | | |
|   Sensor ae30 0000 0000 3290 | 250 | 500 |
| LLU Urgent Care Clinic/Dr. A Kiani | | |
|   Sensor ae30 0000 0000 3290 | 250 | — |
| UCI Urgent Care Clinic/Dr. A. Kiani | | |
|   Sensor ae30 0000 0000 3290 | 250 | — |
|   Sensor ae30 0000 0000 3290 | 250 | |
| Hoag Urgent Care Clinic/Dr. A. Kiani | | |
|   Sensor ae30 0000 0000 3290 | 250 | — |
| UCSF Urgent Care Clinic/Dr. Talke | | |
|   Sensor ae30 0000 0000 3290 | 250 | — |
| UCLA Care Clinic/Dr. Achild | | |
|   Sensor ae30 0000 0000 3290 | 250 | — |
| USC Care Clinic/Dr. Okaydokey | | |

[ Create and Notify Customer ]

Spot Check Credit Download

200 Credits for:
Sensor ae30 0000 0000 3290

Create New Customer Account | My Customers | Issue Credits | Notify All Customers

Credit File

200 Credits Sensor ae30 0000 0000 3290

Note: Click on file to drag and drop onto your desktop. This file will only work on the above listed sensor. Please be advised that if another spot check credit file is generated for this sensor and installed prior to this file, it will void this file being successfully used on this sensor.

Go Back | Create and Notify Customer

FIG. 18B

Spot Check Credits

Your sales rep issues credits after you request either through email, phone or this web site. Click on the file to begin downloading if an active X appears accept the download file.

| Credits Available | Request Additional for a Sensor | # of Credits |
|---|---|---|
| 200 Credits<br>Sensor ae30 0000 0000 3290 | Sensor aee2 3000 0000 0931 | ___ |
| | Sensor aee2 3000 0000 0931 | ___ |
| | Sensor aee2 3000 0000 0931 | ___ |

Tabs: Welcome | Spot Check Credits | Request Equipment | Software Update | Help

[Submit]

SPOT CHECK MONITOR CREDIT SYSTEM

PRIORITY CLAIM TO RELATED PROVISIONAL APPLICATIONS

The present application is a continuation of U.S. application Ser. No. 12/882,111, filed Sep. 14, 2010, titled Spot Check Monitor Credit System, which claims priority benefit under 35 U.S.C. §119(e) to U.S. Provisional Patent Application Ser. No. 61/242,384, filed Sep. 14, 2009, titled Medical Device Life Monitor, U.S. Provisional Patent Application Ser. No. 61/242,792, filed Sep. 15, 2009, titled Spot Check Pulse CO-Oximetry; U.S. Provisional Patent Application Ser. No. 61/352,361, filed Jun. 7, 2010, titled Spot Check Credit System; U.S. Provisional Patent Application Ser. No. 61/354,251, filed Jun. 13, 2010, titled Spot Check Credit System; and U.S. Provisional Patent Application Ser. No. 61/382,812, filed Sep. 14, 2010, titled Advanced Spot Check Monitor. The present application also claims priority benefit under 35 U.S.C. §119(e) to U.S. Provisional Patent Application Ser. No. 61/352,345, filed Jun. 7, 2010, titled Photocommunicative Key for Communicating Payment, Credit, or Other Information to A Patient Monitor. All of the aforementioned applications are hereby incorporated by reference herein in their entirety.

BACKGROUND OF THE INVENTION

Pulse oximetry is a widely accepted noninvasive procedure for measuring the oxygen saturation level of arterial blood, an indicator of a person's oxygen supply. A typical pulse oximetry system utilizes a sensor applied to a patient tissue site. The sensor has emitters that transmit optical radiation having red and infrared (IR) wavelengths into the tissue site. A detector responds to the intensity of the optical radiation after attenuation by pulsatile arterial blood flowing within the tissue site. Based on this response, a processor determines measurements for oxygen saturation and pulse rate. In addition, a pulse oximeter may display a plethysmograph waveform, which is a visualization of blood volume change within the illuminated tissue caused by the pulsatile arterial blood flow over time.

Pulse oximeters capable of reading through motion induced noise are available from Masimo Corporation ("Masimo") of Irvine, Calif. Moreover, portable and other pulse oximeters capable of reading through motion induced noise are disclosed in at least U.S. Pat. Nos. 6,770,028, 6,658,276, 6,157,850, 6,002,952 5,769,785, and 5,758,644, which are assigned to Masimo and are incorporated by reference herein. Corresponding low noise sensors are also available from Masimo and are disclosed in at least U.S. Pat. Nos. 6,985,764, 6,813,511, 6,792,300, 6,256,523, 6,088,607, 5,782,757 and 5,638,818, which are assigned to Masimo and are incorporated by reference herein. Such reading through motion pulse oximeters and low noise sensors have gained rapid acceptance in a wide variety of medical applications, including surgical wards, intensive care and neonatal units, general wards, home care, physical training, and virtually all types of monitoring scenarios.

Noninvasive blood parameter monitors capable of measuring blood parameters in addition to $SpO_2$, such as HbCO, HbMet and total hemoglobin (Hbt) and corresponding multiple wavelength optical sensors are also available from Masimo. Noninvasive blood parameter monitors and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Masimo Laboratories, Irvine, Calif. (Masimo Labs) and both incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare®, Rad-9® Rad-5®, Rad-5v™ or PPO+® Masimo SET® pulse oximeters, are all available from Masimo. Physiological monitoring systems including multiple wavelength sensors and corresponding noninvasive blood parameter monitors, such as Rainbow® adhesive and reusable sensors and RAD-57™ and Radical-7™ monitors for measuring $SpO_2$, pulse rate, perfusion index, signal quality, HbCO and HbMet among other parameters are also available from Masimo.

Unlike the foregoing traditional pulse oximeters, many monitoring environments, such as, for example, hospital, caregiver, fitness, home care, self monitoring or the like, expense care on a consumption basis. For example, when a caregiver uses a disposable medical product, such as a needle, bandage, etc., the caregiver bills an amount associated with the disposable product to the payor of the patient's care, whether that be a government entity, private entity, or the patient themselves. In the case of sophisticated electronic medical instruments, many sensors thereof include disposable parts, and billing is similarly accomplished by tracking use of that disposable part and associating its use with a payor of the patient's care.

SUMMARY OF THE INVENTION

However, many other monitoring devices may lack single use disposable parts or other straightforward mechanisms of accounting for device use with a particular patient. Such difficulties are exacerbated when the caregiver extends or would have to extend large resources to acquire and/or maintain such monitoring equipment.

Additionally, as monitors become more sophisticated and digital data such as demographic information, monitoring history including trending, or even information about what is being monitored becomes more prevalent, storage of such digital data on specific devices may be a manner in which potentially sensitive information can remain more confidential, private or at least in better patient control.

Based on at least the foregoing, the present disclosure includes systems, apparatuses, methods and devices addressing these and other shortfalls of the prior art. In various embodiments, the disclosure herein includes a physiological measurement system has a sensor that transmits optical radiation at a multiplicity of wavelengths other than or including the red and infrared wavelengths utilized in pulse oximeters. The system also has a processor that determines the relative concentrations of blood constituents other than or in addition to $HbO_2$ and Hb, such as carboxyhemoglobin (HbCO), methemoglobin (MetHb), fractional oxygen saturation, total hemaglobin (Hbt) and blood glucose to name a few. Further, such a system may be combined with other physiological parameters such as noninvasive blood pressure (NIBP).

A spot check monitor is advantageously utilized in conjunction with a physiological measurement system so as to provide a mechanism to inform users that a medical device, such as a sensor, has exceeded its designed service length. The spot check monitor collects information that is specific to each device including information that reflects that a device falls below usage limits set by the manufacturer.

One aspect of a spot check credit system partitions the task of distributing sensor credits between a server functioning as a credit provider and various clients functioning as credit requesters. The server and the clients communicate over a computer network. The server runs a web server program so as to serve web pages to the clients. The clients run web browsers so as to receive the web pages and access spot check credits.

Another aspect of a spot check credit system comprises a server that communicates web pages over a computer network. A client is in communications with the server and executes a web browser so as to receive the web pages. A spot check credit request is relayed from the client to the server via one of the web pages. The request specifies a sensor ID and a number of credits to purchase. Each spot check credit enables a single measurement for a group of physiological parameters. A credit file application executes on the server so as to generate a credit file in response to the spot check credit request. The credit file is downloaded from the server to the client.

In various embodiments, the spot check credit system further comprises a physiological monitor in communications with the sensor so as to perform spot check measurements in conjunction with the sensor. The monitor is in communications with the client so as to download the spot check credit file. In an embodiment, the credit file comprises a file sequence code indicating when the credit file was created relative to other credit files, a file sensor ID identifying a sensor and a number of purchased spot check credits. The sensor has a memory that stores a sensor ID identifying the sensor, a sequence code of the most recent credit file used to add credits to the sensor and a number of remaining spot check credits that is decremented after each spot check measurement. The memory is readable by the monitor so as to determine each of the sensor ID, the sequence code and the remaining spot check credits.

In other embodiments, the monitor has an interface that downloads the sensor memory and uploads credit file data when the sensor is plugged into the monitor. A monitor display shows the sensor ID, the sequence code and the spot check credit number prior to a credit download. A processor compares the credit file with the sensor memory so as to verify the sensor ID and the sequence code. The monitor communicates with the client via at least one of a USB cable interconnecting the monitor and the client and a memory card, which the client and the monitor can be read from and write to. In an embodiment, the flash memory card, such as a MicroSD card, is physically transferred between the client and the monitor for uploads and downloads. The sequence code may be a coordinated universal time (UTC) stamp.

Another aspect to a spot check credit system is a method comprising the steps of specifying a sensor ID; requesting spot check credits for the specified sensor; creating a credit file with a time stamp, the sensor ID and the credits; and encrypting the credit file. The credit file may be downloaded to a client from a server and retransmitted to a monitor connected to the client. The retransmission may be directly via a cable connected between the client and monitor or indirectly via a flash memory card.

In various embodiments, the credit file is decrypted and a sensor attached to the monitor is read so as to verify its sensor ID matches the credit file sensor ID. The sensor is read to determine a sensor time stamp. The credit file time stamp is verified to be later than the sensor time stamp. The credit file credits are added to pre-existing sensor credits.

In other embodiments, a spot check measurement is performed, a decremented credit count is downloaded to the sensor. The spot check results are uploaded to the client. An email address is associated with the spot check results. The results are uploaded to the server along with the email address. The spot check results are stored on a server database. Also, the spot check results are emailed from the server to the given email address.

An aspect of a spot check monitor method is a reusable sensor attached to a spot check monitor so as to upload sensor credits to the sensor. In an embodiment, each sensor credit represents a quantum of currency. The monitor reads the number of sensor credits and is enabled to make a physiological measurement in conjunction with the sensor if the number of sensor credits is greater than zero. After the measurement, the number of sensor credits is decremented. The spot check monitoring method provides a physiological monitor having a sensor port that attaches a reusable sensor. An optical sensor attaches to the sensor port. At least one sensor credit is uploaded from the monitor to store in sensor memory. The sensor credit represents a quantum of currency. The monitor reads the sensor memory so as to determine the number of sensor credits is at least one. The monitor then performs a physiological measurement in conjunction with the sensor based upon a remaining sensor credit. The monitor decrements the sensor memory corresponding with the physiological measurement. In various embodiments different buttons are pressed on the spot check monitor to measure different variables. For example, one button starts a SpO2 measurement and another button starts a SPCO measurement.

BRIEF DESCRIPTION OF THE DRAWINGS

FIG. 7 is a perspective view of another spot check instrument embodiment, including a monitor and corresponding sensor;

FIGS. 8A-C are front, back perspective and bottom views, respectively, of a spot check monitor embodiment;

FIGS. 15-19 are illustrations of spot check credit website pages;

FIG. 15A is a sales manager welcome page;

FIGS. 17A-C are customer and credit management pages for the sales representatives;

FIGS. 18A-B are detailed equipment management and credit download pages for the sales representatives; and FIGS. 19A-D are detailed credit, equipment, software update and tech support pages for the customers.

DETAILED DESCRIPTION OF THE PREFERRED EMBODIMENTS

Figure 1:
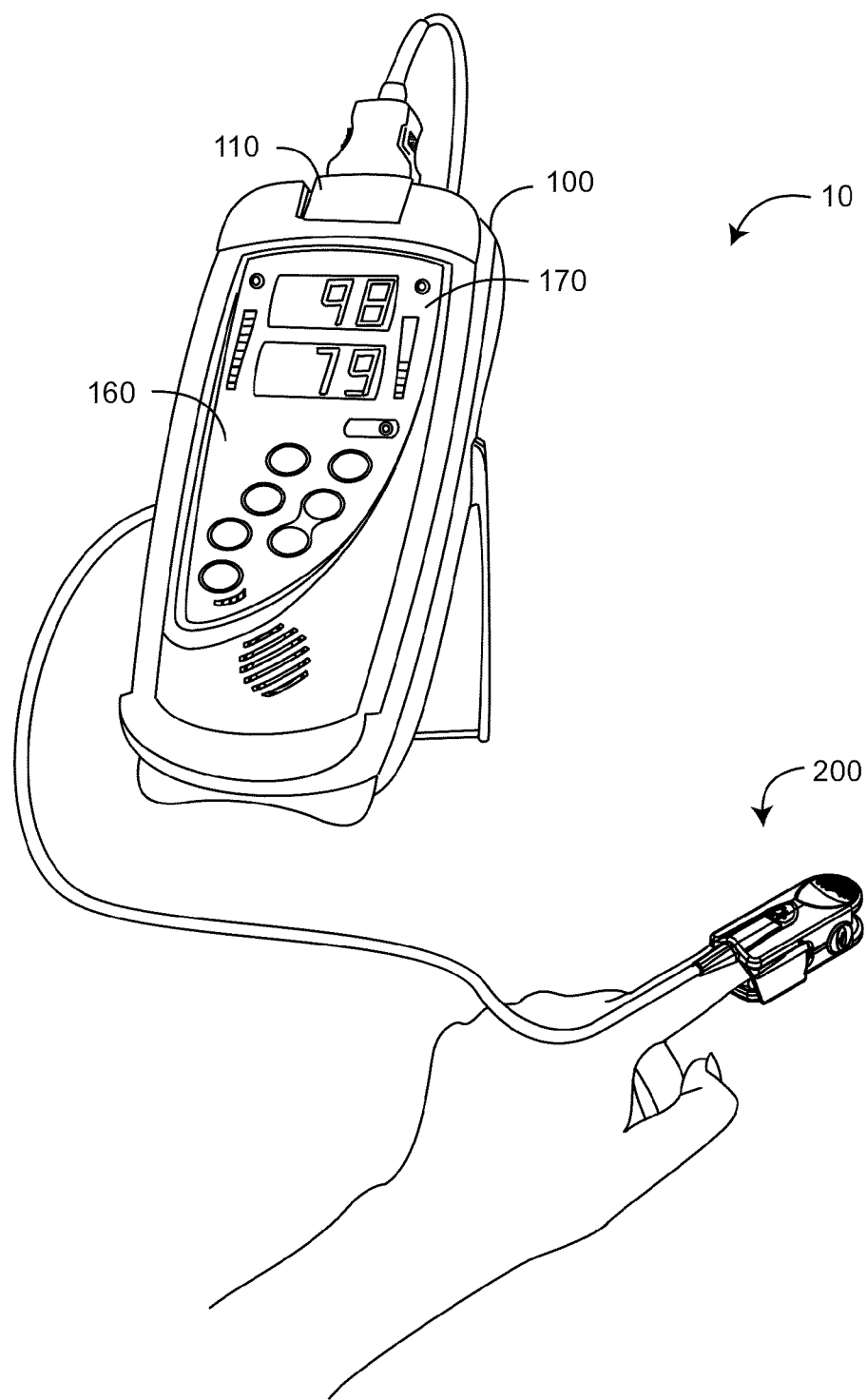
FIG. 1 is a perspective view of a physiological measurement system incorporating reusable sensor and spot check monitor embodiments.

FIG. 1 illustrates a physiological measurement system 10 having a monitor 100 and a reusable multiple wavelength sensor 200 with enhanced measurement capabilities as compared with conventional pulse oximetry. In particular, the multiple wavelength sensor assembly 200 allows the measurement of blood constituent and related parameters in addition to oxygen saturation and pulse rate. Alternatively, the multiple wavelength sensor assembly 200 allows the measurement of oxygen saturation and pulse rate with increased accuracy or robustness as compared with conventional pulse oximetry.

In one embodiment, the sensor assembly 200 is configured to plug into a monitor sensor port 110. A monitor keyboard 160 provides control over operating modes and alarms, to name a few. A display 170 provides readouts of measured parameters, such as oxygen saturation and pulse rate, along with sensor life information, to name a few. The keyboard 160 can be pressed to change a display 170 readout from one parameter to another, such as from percentage oxygen saturation to percentage carboxyhemoglobin, and one parameter readout may be provided in a different color from another parameter readout. An artisan will recognize from the disclosure herein that many types of monitors fall within the scope of this disclosure and that monitor 100 generally can comprise electronic monitoring circuitry to determine or monitor patient information from appropriate sensors communicating with body systems or tissue.

Figure 2:
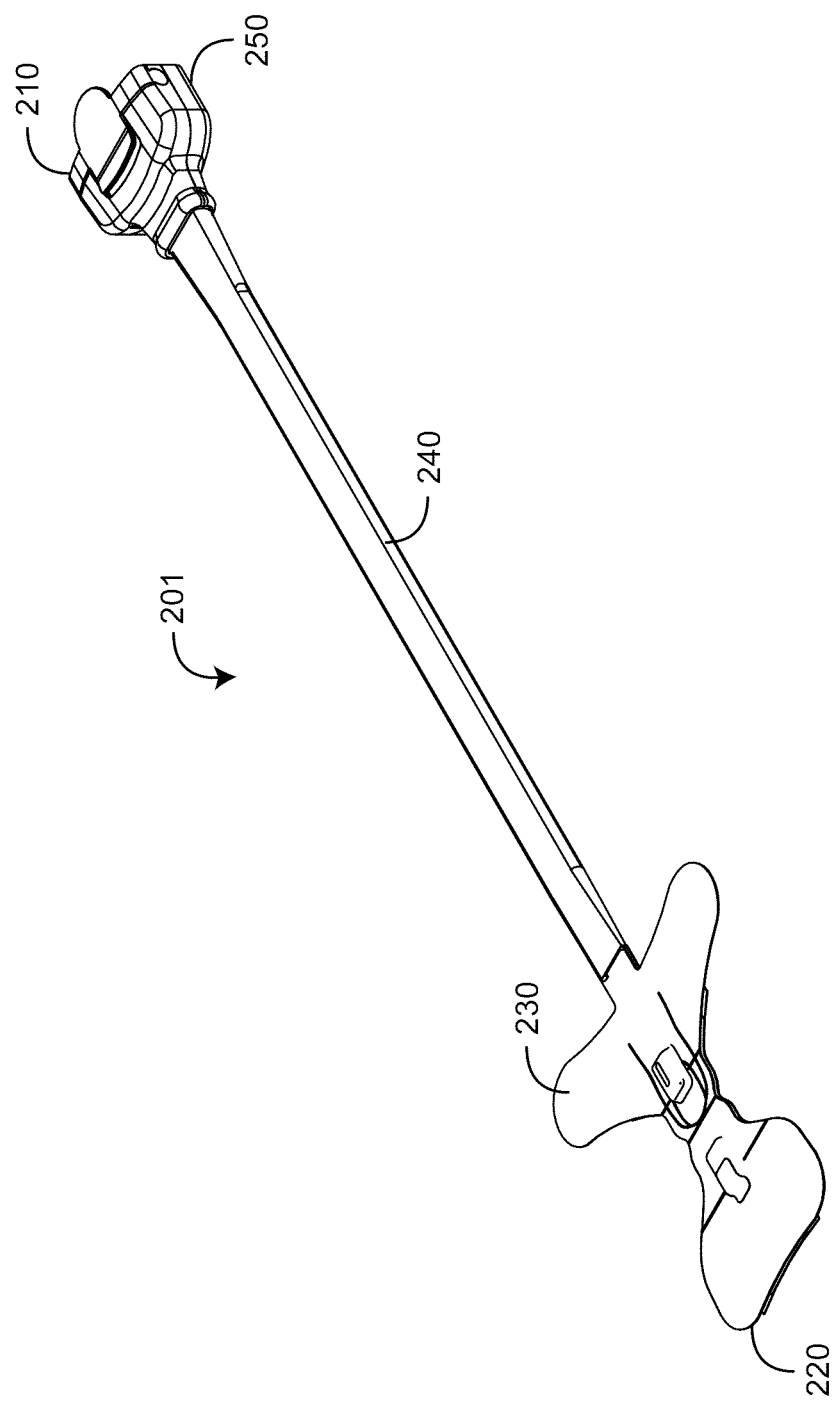
FIG. 2 is a perspective view of disposable sensor embodiment for use with a physiological measurement system.

FIG. 2 illustrates an embodiment of a disposable multiple wavelength sensor 201 configured for finger placement. The sensor 201 has a tape end 220 and an opposite connector end 210 electrically and mechanically coupled via an interconnect 240. The tape end 210 attaches an optical assembly to a tissue site. An emitter transmits light into the tissue site and the detector generates a sensor signal responsive to the transmitted light after tissue absorption. The sensor signal is communicated via the interconnect 240 to the connector 250. The connector 250 mates with a patient cable (not shown) that communicates the sensor signal to a monitor 100 (FIG. 1). The monitor calculates a variety of physiological parameters from the detector signal, such as pulse rate (PR), oxygen saturation (SpO2), carboxyhemoglobin (HbCO), methemoglobin (HbMet) and total hemoglobin (Hbt), to name a few. A sensor configured for measurement of at least some of the above-mentioned physiological parameters is described in U.S. Provisional Application Ser. No. 60/920,474, filed Mar. 27, 2007, titled Disposable Multiple Wavelength Optical Sensor, and U.S. Provisional Application Ser. No. 60/923,630, filed Apr. 14, 2007, titled Disposable Multiple Wavelength Optical Sensor, both applications incorporated by reference herein.

Figure 3:
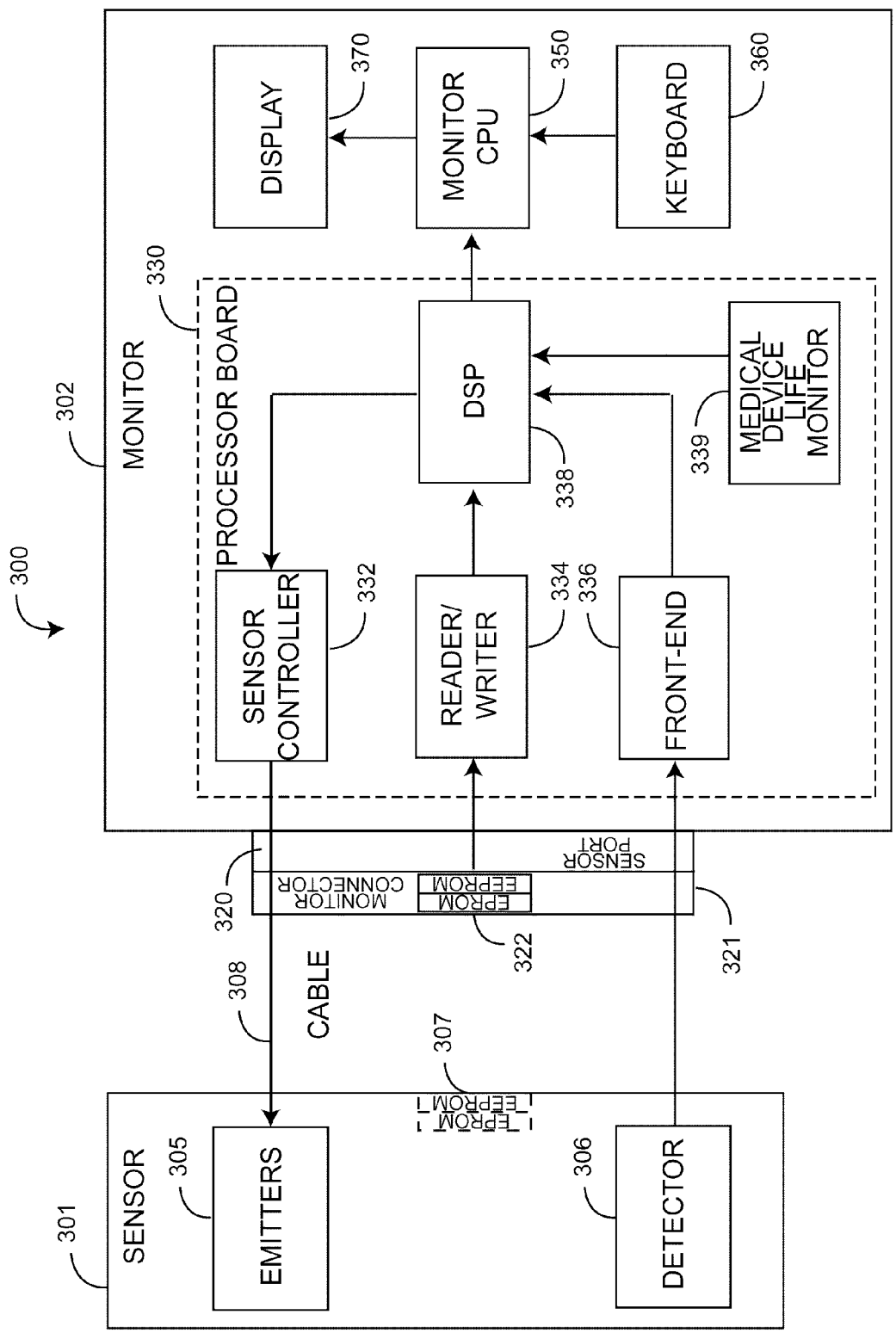
FIG. 3 is a block diagram of a physiological measurement system incorporating a spot check monitor.

FIG. 3 illustrates a physiological measurement system 300 incorporating a medical device life monitor 339. A sensor 301 houses emitters 305 responsive to drivers within a sensor controller 332 so as to radiate light having a multiplicity of wavelengths. The sensor 301 also houses a detector 306 that provides a detector signal responsive to the emitted light after absorption by pulsatile blood flow within a tissue site. The detector signal is filtered, amplified, sampled and digitized by the monitor front-end 336 and input to a DSP (digital signal processor) 338, which also commands the sensor controller 332. The cable 308 electrically communicates drive signals from the monitor's sensor controller 332 to the sensor emitters 305 and a detector signal from the detector 306 to the monitor front-end 336. The monitor connector 321 plugs into the sensor port 320. Medical device life monitor 339 firmware executes on the DSP 338 so that the processor board 330 may read and modify usage information on sensor memory 307 or information element and or cable memory 322 or information element, as described in further detail below.

In one embodiment, the monitor connector 321 houses the information element 322, such as memory or other active or passive electrical component. In a particular embodiment, the information element 322 is an EPROM, or other programmable memory, or an EEPROM, or other reprogrammable memory, or combinations thereof. In an alternative embodiment, an information element 307 is housed within the sensor 301, or an information element is housed within both the monitor connector 321 and the sensor 301. A reader/writer 334 inputs the information element 322 data to the DSP 338 for reference and modification by the medical device life monitor 339 according to sensor usage.

In one embodiment, the DSP 338, controller 332, front-end 336 and reader/writer 334 are a portion of a processor board 330 incorporated into the monitor 302. The processor board 330 communicates with a monitor CPU 350, which processes keyboard 360 inputs and provides display 370 outputs, including physiological parameters and sensor life usage calculated by the DSP 338.

Figure 4:
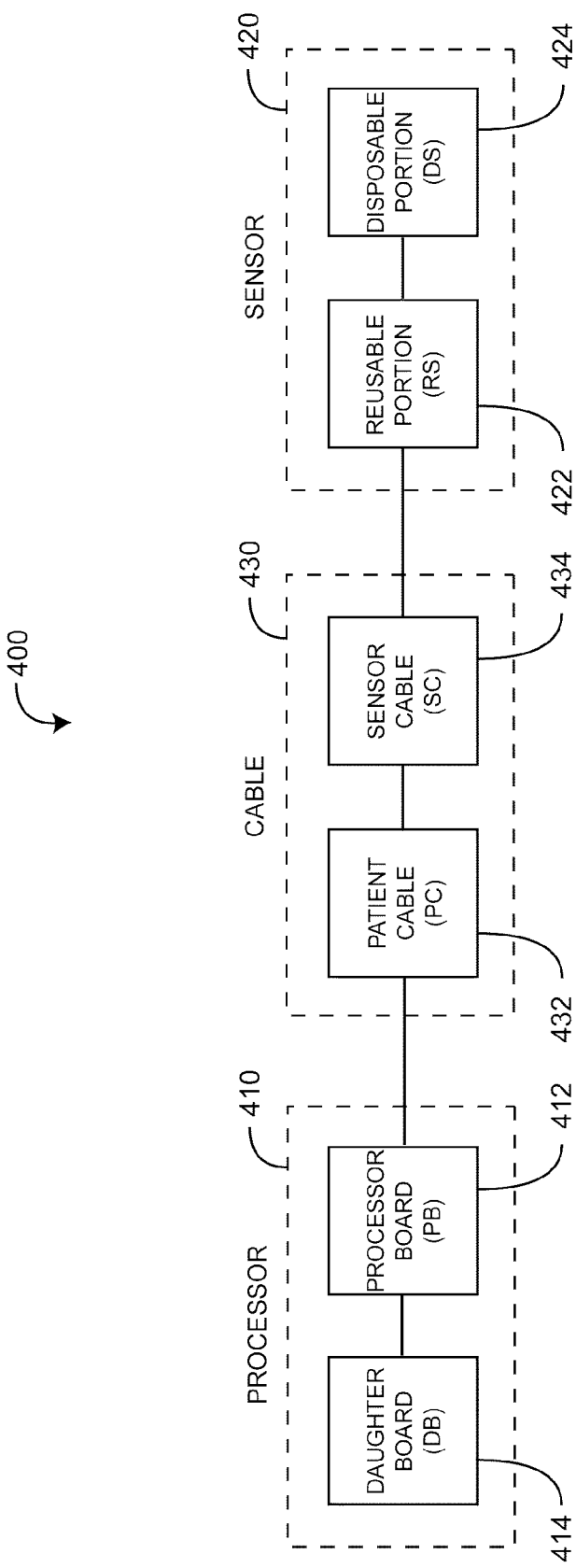
FIG. 4 is a detailed block diagram of a physiological measurement system embodiment wherein each board, cable or sensor portion can have preset medical device life data that is updated with use.

FIG. 4 illustrates physiological measurement system 400 embodiment having processor 410, sensor 420 and cable 430 components. In one embodiment, the processor 410 has a processor printed circuit board "board" 412 and an optional daughter board 414, which plugs into and expands the functionality of the processor board 412. For example, the daughter board 414 may be a noninvasive blood pressure (NIBP) controller that communicates with a blood pressure sensor and the processor board 412 so as to measure blood pressure parameters, or in other embodiments, may include an acoustic respiration controller or the like.

Also shown in FIG. 4, in one embodiment the sensor 420 is a "resposable" sensor comprising a reusable portion 422 and a disposable portion 424. In a particular embodiment, the reusable portion has at least one of a reusable emitter portion and a reusable detector portion, and the disposable portion 424 has at least one of a disposable emitter portion, a disposable detector portion and a disposable tape for attaching the reusable sensor 422 to a tissue site. A resposable sensor is described in U.S. Pat. No. 6,725,075 entitled Resposable Pulse Oximetry Sensor, assigned to Masimo Corporation and incorporated by reference herein.

Further shown in FIG. 4, in one embodiment the cable 430 is a patient cable 432 or a sensor cable 434 or a combination of a patient cable 432 and a sensor cable 434. A sensor cable 434 is fixedly attached at one end to a sensor and has a connector at the other end for attaching to a monitor or a patient cable. A patient cable 434 has connectors at both ends for interconnecting a sensor or sensor cable to a monitor. In an advantageous embodiment various ones of the processor 410, sensor 420 and cable 430 have memories or information elements storing device life data that can be read and modified by a processor board DSP so as to monitor and control usage and life of these respective physiological measurement system components.

Figure 5:
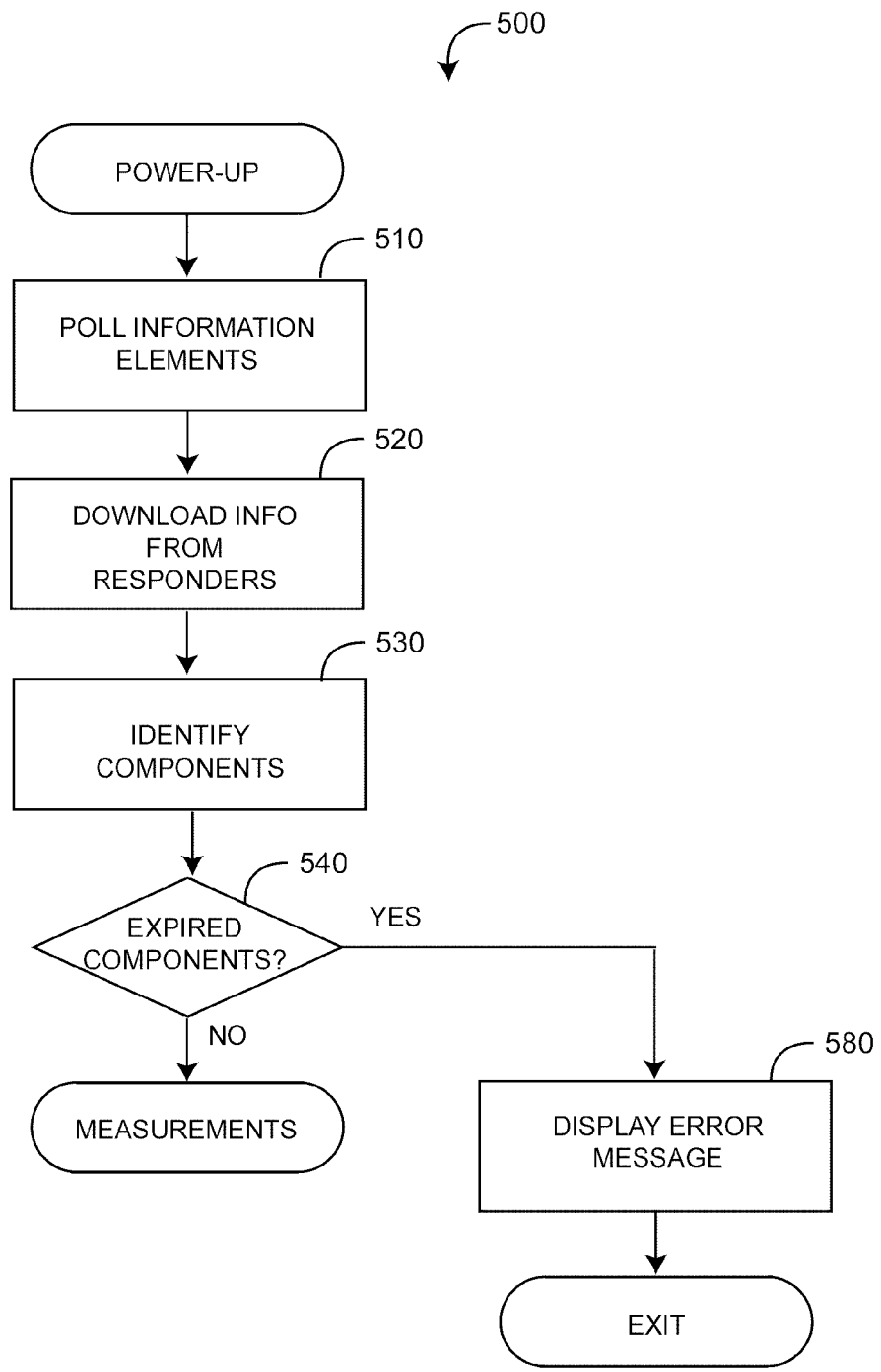
FIG. 5 is a flowchart of a physiological measurement system configuration process including spot check credits.

FIG. 5 illustrates a configuration process 500 for a physiological measurement system executed by a DSP 338 (FIG. 3) with respect to information elements. After system power-up, any information elements are polled 510 so they identify themselves. Information is then downloaded from the responding information elements 520. In one embodiment, download information can be some or all of Identification (ID), Life and Parameters, to name a few. ID identifies a component, the type of component generally, such as a sensor or cable, or a particular part number, model and serial number, to name a few. As another example, ID for a disposable sensor portion may be an attachment location on a patient and ID for a reusable sensor portion may be a patient type. Life, for example, may be a predetermined counter written into an EEPROM to indicate the number of uses or the length of use of a particular component. Then, Life is counted down, say each time power is applied, until a zero value is reached, indicating component expiration. Parameters specifies the measurements the component is capable of supporting, which may include, for example, one or more of SpO$_2$, HbCO, MetHb, fractional SpO$_2$, Hbt, NIBP and blood glucose to name just a few. With respect to a sensor, Parameters depend on the number of emitters, emitter wavelength and emitter configuration, for example. For a cable, Parameters depend on the number of conductors and connector pinouts, for example. Parameters may also simply reflect a license to use a component, such as disposable tape, with respect to a particular system configuration.

As shown in FIG. 5, components are identified 530 from downloaded ID information. If any of the information elements provide Life information, a check is made to determine if the corresponding component is expired 540. If so, an error message is displayed 580. The message may be a warning to replace the component or it may indicate that the system is nonfunctional.

Figure 6:
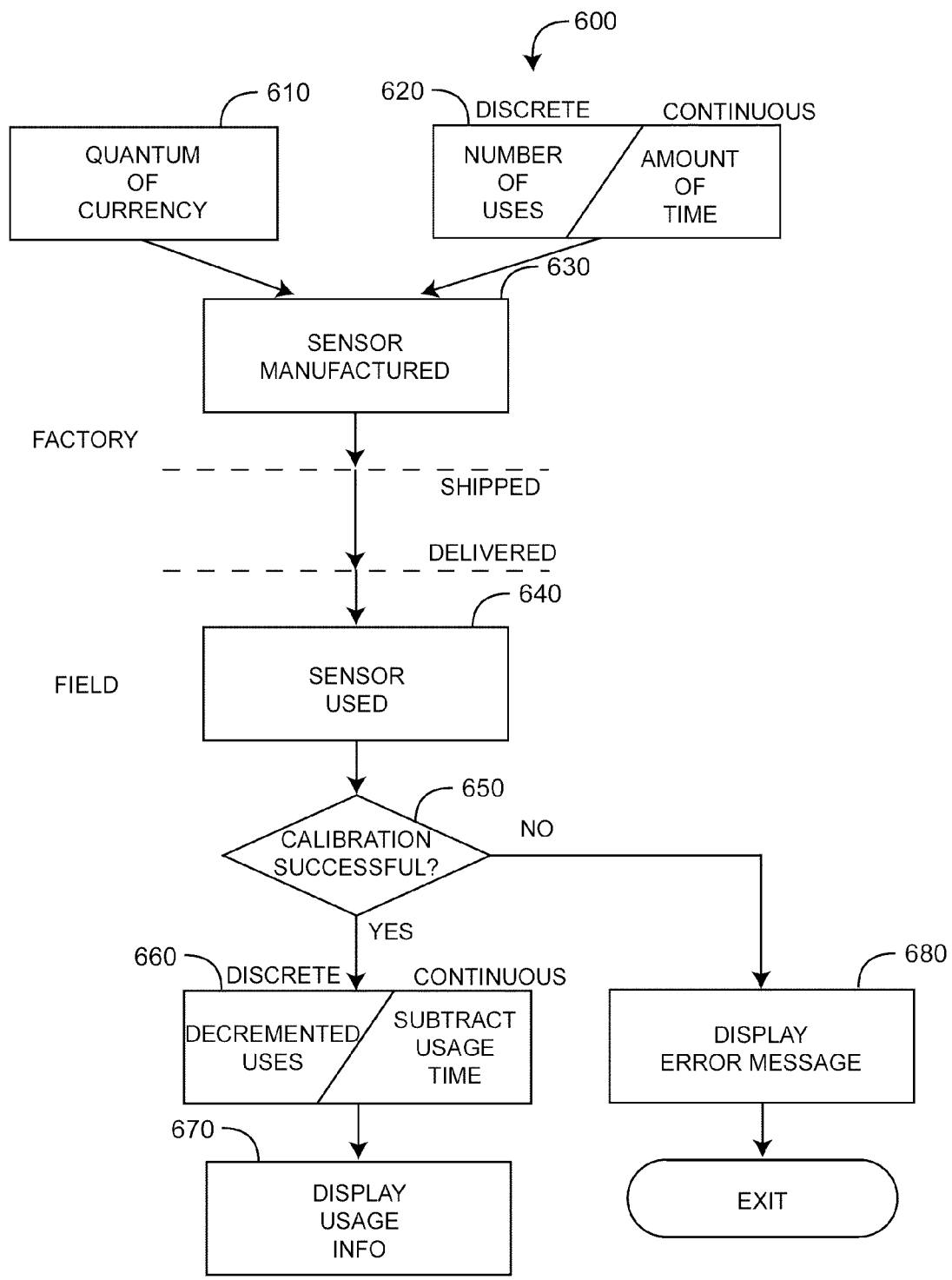
FIG. 6 is a flowchart of medical device spot check process.
Figure 9A:
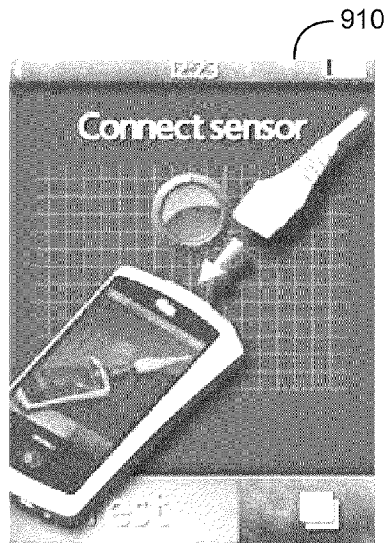
FIGS. 9A-D are screen shots illustrating the steps for making a spot check measurement.
Figure 9B:
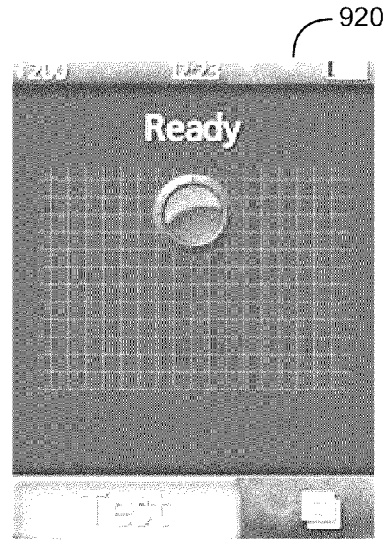
Figure 9C:
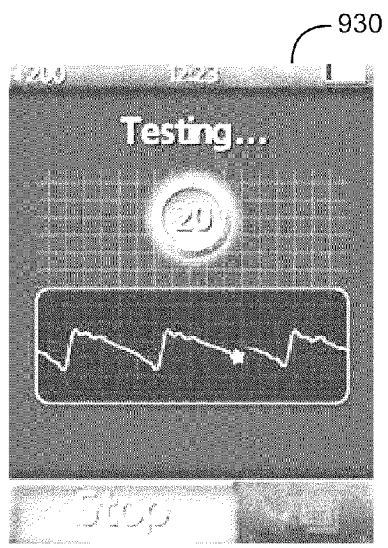
Figure 9D:
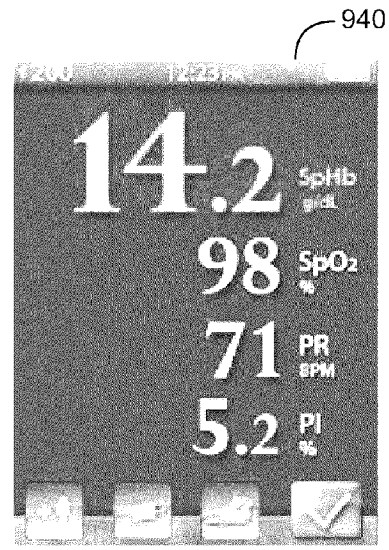

FIG. 6 illustrates a spot check monitor credit process 600 where a quantum of currency 610 is defined, specifying a price per use or per unit time. A sensor life is defined according to the permitted number of uses or amount of usage time 620 for a spot check monitor or continuous monitor, respectively. The sensor is manufactured 630 accordingly, e.g. with the sensor life 620 information stored in a sensor memory or information element. The sensor is then shipped and delivered to an end user. If calibration is successful 650, as the sensor is used 640, sensor life 660 is subtracted, either by decrementing the allotted number of uses or by subtracting usage time. Remaining sensor life is shown on the corresponding monitor display 670. If calibration fails, usage is not debited and an error message is displayed 680.

In various embodiments, all spot check monitor information fits within the memory space of the supported EEPROM memory parts. The spot check monitor provides support to expire an accessory device when the designed service length for the device has been reached. The spot check monitor contain configurable spot check monitor functions that determine how the spot check monitor information collected will apply to the life of the accessory device. The spot check monitor contains a configurable life limit. The spot check monitor configuration contains a configurable percentage at which a near expiration exception can be set. The information collected by the spot check monitor is configurable. A spot check monitor information update period specified in minutes can be configurable in the spot check monitor configuration. The spot check monitor may provide a configurable minimum connection time increment for a device to technology board connection event. The expiration of a spot check monitor device can be checked and reported when the following events occur in the system: The spot check monitor device is initially connected to a processor board. The system is in an off-patient condition and the configured grace period has elapsed in the system.

The spot check monitor grace period maybe be configurable in the spot check monitor. When the spot check monitor device does not configure a grace period the spot check monitor may default to a value of 5 minutes. The spot check monitor can report the life left and the life limit in minutes when requested by a host system. The spot check monitor can support a secondary expiration mode that uses device use counts or a spot check and hourly usage based on a specific parameter being calculated in the system.

In various embodiments, a spot check monitor collects and stores the number of times a spot check monitor device has been used for a spot check for the sensor spot check monitor device. The spot check monitor may support a configurable spot check window, defined in seconds or other units of currency, measure, time or use, where the device can be used to display multiple measurements of a parameter and only increment a spot check count once. In an embodiment, the spot check window configuration may have a range from 0 to 30 minutes. The spot check monitor may support a configurable charge per spot check, defined in pennies or other units of currency (U.S. or foreign or may calculate exchange by any of a wide variety of known methods), measure, time or use, that is applied to the configured life limit of the spot check monitor device. In an embodiment, the charge per spot check may have a range from 1 to 65,536 ($655.36) pennies. The spot check monitor may collect and store the hourly usage, in minutes, of a parameter. The hourly usage of a parameter may be collected and stored separately from the life monitor run time. The charge per minute, defined in pennies, may be configurable in the life monitor configuration. The charge per minute may have a range from 1 to 65,536 ($655.36) pennies.

In various embodiments, the spot check monitor parameters are one or more of noninvasive SpHb, SpMet, SpO2, SpCO, although many other parameters may advantageously be included. For example, other blood constituents, parameters or analytes, may include a percent value for arterial carbon monoxide saturation ("HbCO"), a percent value for methemoglobin saturation (a brownish-red form of hemoglobin that cannot function as an oxygen carrier) ("HbMet"), total hemoglobin ("HbT"), fractional SpO$_2$ ("SpaO$_2$") or the like. Additionally, caregivers often desire knowledge of HbO$_2$, Hb, blood glucose ("HbGu"), water, the presence or absence of therapeutic drugs (aspirin, Dapson, nitrates, or the like) or abusive/recreational drugs (methamphetamine, alcohol, steroids, or the like), concentrations of carbon dioxide ("$CO_2$"), oxygen ("$O_2$"), pH levels, bilirubin, perfusion quality, albumin, cyanmethemoglobin, oxygen content ("CaO2"), and sulfhemoglobin ("HbSulf"), signal quality, respiration, sedation, combinations of the same or the like. Accordingly, the present disclosure includes a multi-parameter patient monitor capable of determining one or more of the foregoing parameters, other than or in addition to, $SpO_2$, plethysmograph waveforms, perfusion quality index, or pulse rate.

In an embodiment, the sensor will not expire during active patient monitoring. During a sensor off condition while the sensor is expired, a certain amount of time may be given to the user to re-apply the sensor. Once measurements have reached the display "Ready" state on the device, a sensor time of 10 minutes or 1 spot check use may be decremented. Sensor may have a defined number of hours of active SpHb monitoring and uses for Spot Checks. Additional checks can be performed within a predetermined number of seconds (~20 sec) from the initial use with no impact to the sensor use time or count. The error message display when Sensor Life Expires may be "Expired Sensor". The display may show sensor time for 120 seconds when sensor is connected to device, applied to a patient or removed from a patient. Spot Check device may utilize a sensor use bar graph. The display may show sensor time with an audible beep when remaining time reaches 4 hr, 2 hr, 1 hr, and 0 min.

FIG. 7 illustrates a spot check instrument 100 embodiment including a handheld monitor 800 and a noninvasive, reusable finger-clip sensor 10 for spot checking of pulse oximetry parameters, such as arterial oxygen saturation ($SpO_2$), pulse rate (PR) and perfusion index (PI) in addition to advanced blood parameter measurements, such as total hemoglobin concentration (SpHb). The spot check instrument 100 is designed for use in hospitals, hospital-type facilities, homes, clinics, physician offices, blood donation facilities and ambulatory surgery centers, to name a few. The spot check instrument 700 advantageously works in conjunction with a spot check credit system that provides online access for purchasing, downloading and renewing sensor credits, with or without intervention of the manufacturer. Sensor credits pay for sensor usage on a spot check basis, where one credit enables a sensor to make a single measurement of a group of predefined parameters, such as those listed above. A blood parameter instrument including a monitor and noninvasive sensor is described with respect to U.S. patent application Ser. No. 12/534,812 titled Multi-Stream Sensor Front Ends For Noninvasive Measurement of Blood Constituents; filed Aug. 3, 2009, assigned to Masimo Laboratories, Inc.; Irvine, Calif. and incorporated by reference herein. A spot check monitor 800 is described in detail with respect to FIGS. 8A-C, below. A spot check measurement process is described in detail with respect to FIGS. 9A-D below. A spot check credit system is described in detail with respect to FIGS. 10-19, below.

FIGS. 8A-C illustrates the spot check monitor 800 having a power button 810, an LCD touchscreen 820, a sensor connector port 830, an earphone jack 840, a MicroSD card slot 850, a mini USB port 860 and a power port 870. The power button 810 is pressed to turn the monitor 800 on or off. The touchscreen 820 is interactive, allowing a user to move through screens, select options, enter information and view instrument specific messages. The sensor connector port 830 connects a reusable sensor 10 to the monitor so as to enable spot check measurements of $SpO_2$, PR, PI and SpHb. The earphone jack 840 allows a user to listen to a parameter or measurement result using an earphone with a standard 3.5 mm plug. The MicroSD card slot 850 accepts a flashcard to upload new software to the monitor 800 or additional spot check credits to an attached sensor 10 (FIG. 7). The mini USB port 860 connects a mini USB-to-USB cable to the USB port on a computer. This allows the computer to download new software or additional spot check credits to the monitor 800 or upload information, such as measurement results, to the computer. The power port 870 connects to an AC/DC converter so as to provide DC power to the monitor 800 and/or charge monitor batteries.

As shown in FIG. 8A, the touchscreen 820 displays the number of spot checks remaining in the attached sensor 821, the time of day 822 and battery status 823, although an artisan will recognize from the disclosure herein many other ways of interacting with the user to indicate the remaining spot checks, including for example, red-yellow-green indicators, separate audio or visual indicators, gas bars, pie charts, graphs, sounds, colors, fillable or drainable icons, combinations of the same or the like. The touchscreen 820 also displays measured parameter values 824, such as total hemoglobin, oxygen saturation, pulse rate and perfusion index, as shown. The touchscreen 820 also has "soft key" buttons 825 that have various functions according to displayed icons. These functions may include "start a test," "go to the main menu screen," "submit inputs," "move back a screen," "exit a screen," "scroll up/down a list or page," "display an interactive dialogue for user options" or "add patient specific information," to name a few.

To determine if a reusable sensor 10 (FIG. 7) contains spot check credits, it is connected to the monitor 800. A numeric value will appear in the top left corner of the screen 821, with the number of available spot check credits it contains (e.g. 20). If one or more credits remain, "Ready" is displayed on the screen 820. If no spot checks remain, the screen 820 will show 0 credits in the upper left corner 821 in red and the message "No Spot Check Credits."

FIGS. 9A-D illustrates the steps for making a measurement with the spot check instrument 700 (FIG. 7). The spot check sensor 10 (FIG. 7) is attached to the monitor's sensor port 830 (FIG. 8A). The power button 810 (FIG. 8A) is pressed. The monitor 800 (FIG. 8A) generates an audible tone and displays a logo screen (not shown). If a sensor is not attached or not connected completely, the monitor displays a "connect sensor" screen 910. Once a sensor is correctly connected, the monitor displays "ready" screen 920, indicating that a spot check test may proceed. Touching the display screen 820 (FIG. 8A) initiates the test. The monitor displays a "testing" screen 930 while the test is running, which includes a timer that counts down the seconds until the test is complete. If motion is detected during testing, a motion bar at the bottom of the screen will begin to fill. If the entire bar is full, the test will fail as a result of too much motion. After a successful spot check test, the monitor generates an audible tone and displays a result screen 940 showing various parameter values. Further, after the test detailed information about a patient can be entered by touching the appropriate soft key. If printer or email options are set up, a printer and/or email soft key will appear at the bottom of the screen allowing the test results to be sent to a designated printer or email address according to on-screen instructions.

Figure 10:
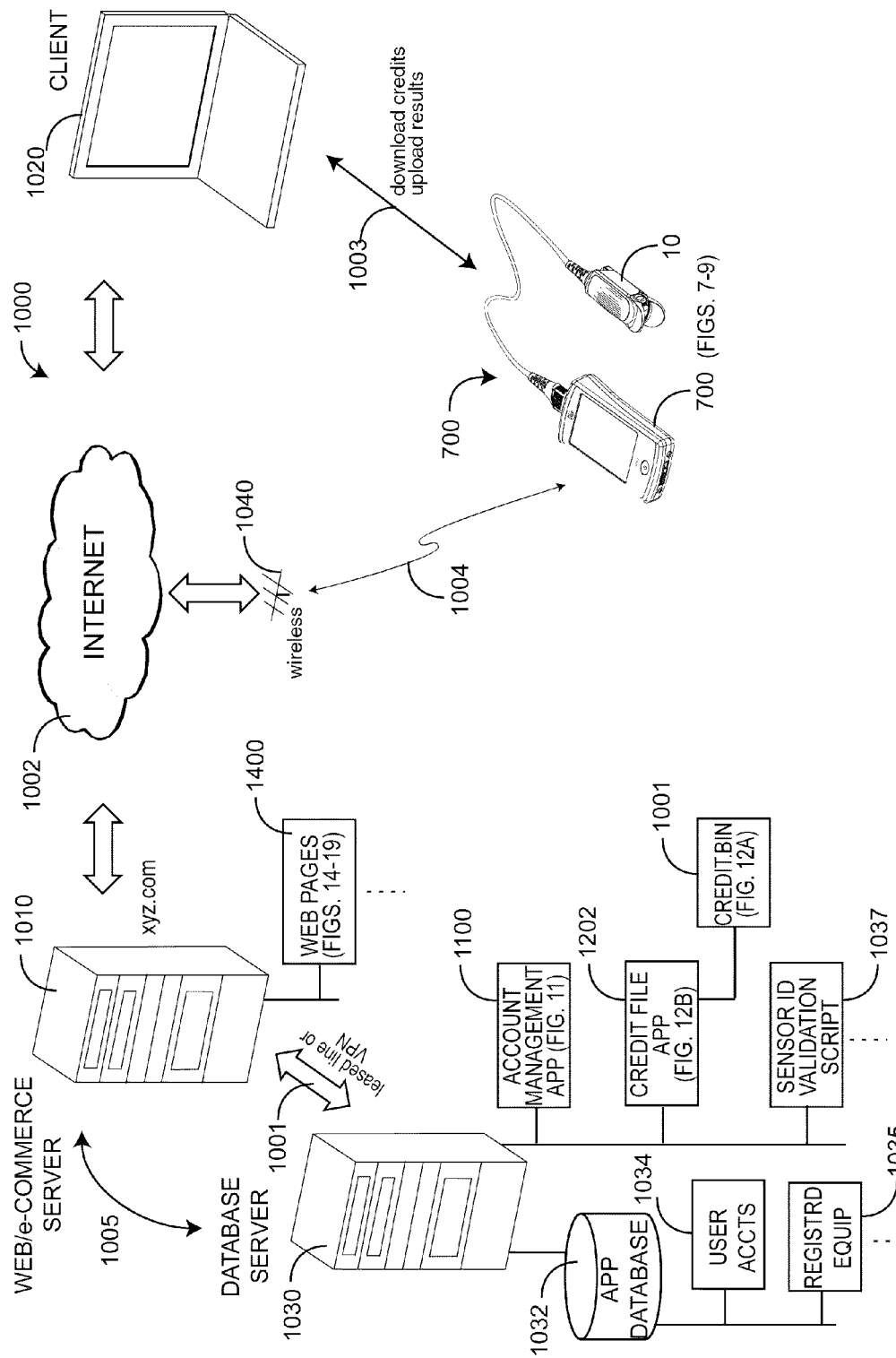
FIG. 10 is a system diagram of a spot check credit system.

FIG. 10 illustrates a spot check credit system 1000 having a server 1005, web pages 1400, an account management application 1100, a credit file application 1202 that generates credit files 1201, a sensor ID validation script 1037 and an application database 1032 that includes information regarding user accounts 1034 and registered equipment 1035. The spot check credit system 1000 communicates with multiple "clients" 1020 via the Internet 1002. Clients 1020 may be any of various devices such as PCs, laptops, smart phones and various e-readers/pads to name a few. Clients 1020 access the Internet via cable, DSL or fiber-optics or via wireless technology including Wi-Fi, EV-DO, HSPA, WiMax, LTE or other cellular and satellite technologies to name a few. Clients 1020 may be in communications with spot check instruments 700 including spot check monitors 800 and corresponding sensors 10, such as described with respect to FIGS. 7-9, above. One advantageous aspect of the spot check credit system 1000 is interactive online instrument management, sales and support related to spot check blood parameter measurements. Various functions of a spot check credit system 1000 include spot check credit purchase and download; spot check test data and device status upload, such as raw data, use statistics and trends; software updates; purchase of equipment and accessories, including discounts and specials; sales and account management; training and technical support, including live help, videos, manuals and documents; related health management news; and feedback, including testimonials, surveys and issues; to name a few.

In an upload embodiment, a user option offers a choice of emailing spot check test results to engineering support for the analysis of successful and unsuccessful tests. In another upload embodiment, when a monitor 800 is connected to a client 1020, the monitor 800 uploads a copy of all spot check test results. Corresponding monitor status, if any, is also uploaded. The test results advantageously have all patient identifying data removed, or include a wide variety of mechanisms for dealing with patient data which may be confidential or otherwise regulated by the caregiver, business concern, the government, or combinations of the same. The client 1020 then uploads the test results to the server 1005 for manufacturer analysis. In yet another upload embodiment, when a monitor 800 wirelessly connects 1004 directly to the server 1005, test results and any corresponding monitor data is uploaded to the server 1005 prior to, concurrently with or subsequent to transferring credits, software updates or other downloads to the monitor. Uploaded monitor data may include raw sensor data, processed waveform data, use statistics, such as how many tests are administered, test time of day and the number and time of monitor power-ups, to name a few. A spot check credit system advantageously allows teams from engineering, clinical research or marketing to collaborate online to process and review collected uploads to determine trends, statistics and variables in patient demographics, instrument use, signal processing algorithm behavior and raw sensor data for use in engineering development, client management and patient management, as examples.

As shown in FIG. 10, the server 1005 provides web pages 1400 to the clients 1020 at a predetermined web site address (generically denoted "xyz.com" herein). The account management application 1100 determines the website functionality in response to client inputs. The credit file app 1202 generates a credit file 1201, which includes a sensor ID verified by the validation script 1037. The user accounts 1034 and details of registered equipment 1035, including monitors and sensors, are stored on the database 1032 among other data.

Also shown in FIG. 10, a particular advantageous aspect of the spot check credit system 1000 is a website for the purchase and online delivery of sensor credits. A purchased credit file 1201 containing a specified number of credits is downloaded to a client device 1020, and then to a spot check monitor 800, which loads the credits into the sensor 10. Measurement results may be uploaded as reports to the client 1020 and advantageously delivered to an arbitrary email address via the server 1005. In another embodiment, credits are wirelessly downloaded 1004 directly from the server 1005 to a spot check monitor 800 and reports are wirelessly uploaded directly from the monitor 800 to the server 1005, bypassing the client computer or device. Account management 1100 is described in further detail with respect to FIG. 11, below. Credit files 1201 and credit file downloads are described in further detail with respect to FIGS. 12A-B, below. Web pages 1400 are described in further detail with respect to FIGS. 14-19, below.

Although a server 1005 is described above as a unified device at a specific location, in other embodiments the server 1005 comprises a web server 1010 distinct from the database server 1030. In an advantageous embodiment, the web server 1010 is located at any of various commercial server "farms." The database server 1030, however, is located at a private, secure location, such as corporate headquarters so as to more easily protect sensitive customer, sales and patient information. In such an embodiment, the database server 1030 communicates with the web server 1010 over a leased line, a virtual private network or other secure communications link.

Figure 11:
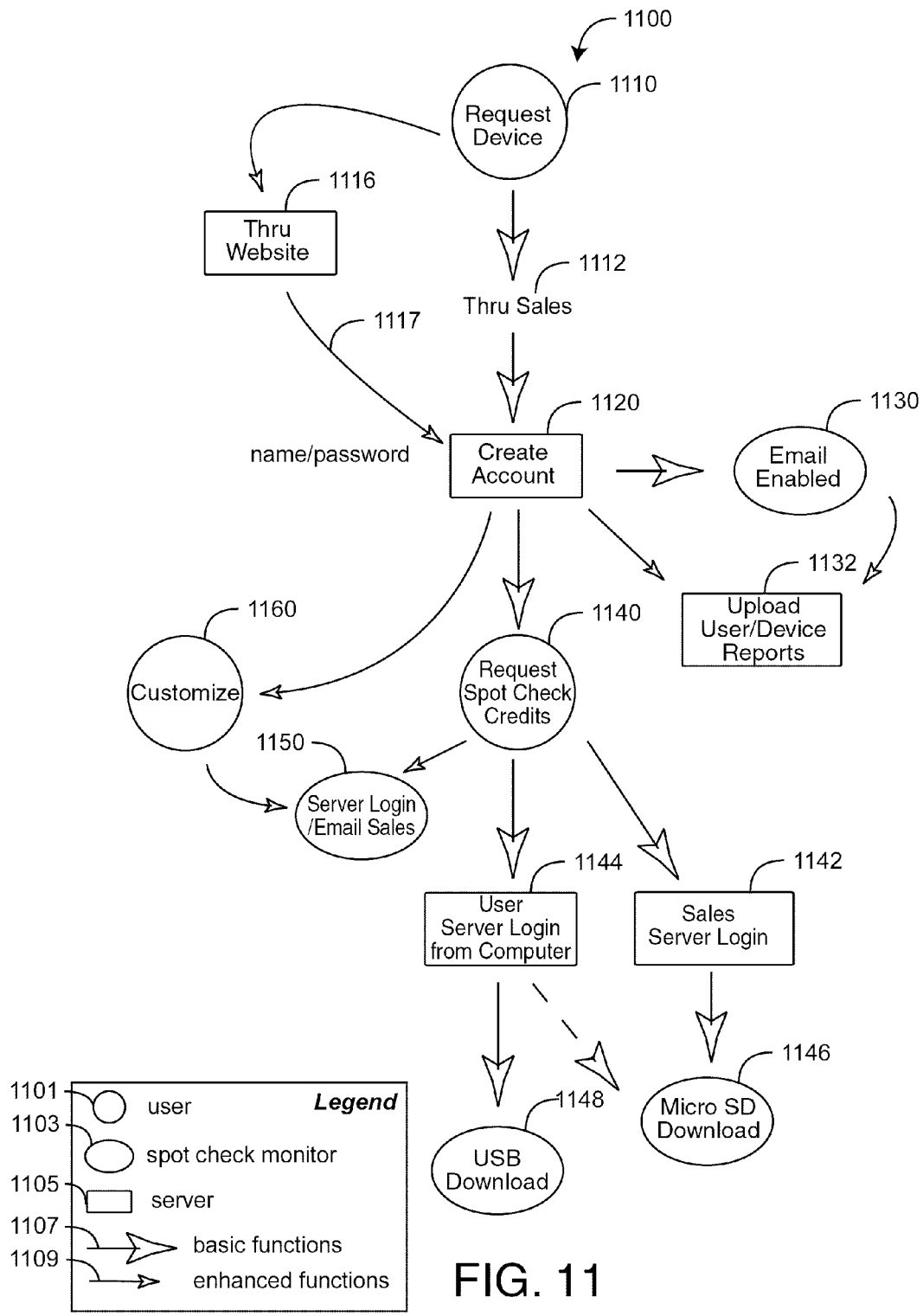
FIG. 11 is a functional flow diagram of a spot check credit process.

FIG. 11 illustrates a spot check credit process 1100 showing interaction between a user 1101, a monitor 1103 and the spot check web server 1105 or sales staff in terms of basic functions 1107 and enhanced functions 1109. A user may request a device 1110, including a monitor 800 (FIG. 7) or sensor 10 (FIG. 7), via sales 1112 or via a spot check credit website 1116. A web account is created 1120 accordingly, either by the sales staff 1112 or directly from the website 1116, providing the user with a name and password 1117 so as to access the account.

As shown in FIG. 11, a web account advantageously enables email 1130 on the monitor. This allows the user to upload user information and device reports 1132 to any user computing device, such as a PC, smart cell phone, PDA or electronic pad. In an embodiment, the user provides any email address, which is stored on the server 1105 (FIG. 11). In various embodiment and for security concerns, email can be routed to the server, which then relays it to the user-provided address.

Also shown in FIG. 11, a particularly advantageous function of the spot check credit process 1100 is to facilitate the purchase and delivery of spot check credits to a sensor. A web account 1120 allows the user to purchase spot check credits for a sensor online. A user requests spot check credits 1140 for a sensor in several ways. The user can login to the spot check web site 1144 from any computer with Internet access, as described with respect to FIG. 10, above. The credits are purchased by credit card, invoice or other well-known payment methods. The server responds by downloading a credit file, as described with respect to FIGS. 12A-B, below. The credit file is transferred to the monitor directly via USB cable 1148 or indirectly by writing the credit file onto a MicroSD card 1146. Once loaded, the MicroSD card is removed from the computer and inserted into the monitor. Downloading a credit file from the monitor to the sensor is described further with respect to FIGS. 13A-B, below. In another embodiment, a monitor downloads a credit file wirelessly using, for example, a Bluetooth connection to the user computer or a Wi-Fi connection direct to the Internet, without the need for a separate computer, as described with respect to FIG. 10, above.

Further shown in FIG. 11, the user can telephone or otherwise contact sales support. Sales staff can then login to the spot check web site 1142 to purchase credits for the user, download the credit file to a MicroSD card, and ship the card to the user accordingly. A user can also email sales via the monitor 1160 (and attached computer) so as to purchase credits via shipped MicroSD card. Besides sensor credits, the user 1160 can login to the spot check website 1150 so as to customize monitor features including the addition of parameters or the customization of screen and sound interfaces, to name a few.

Figure 12A:
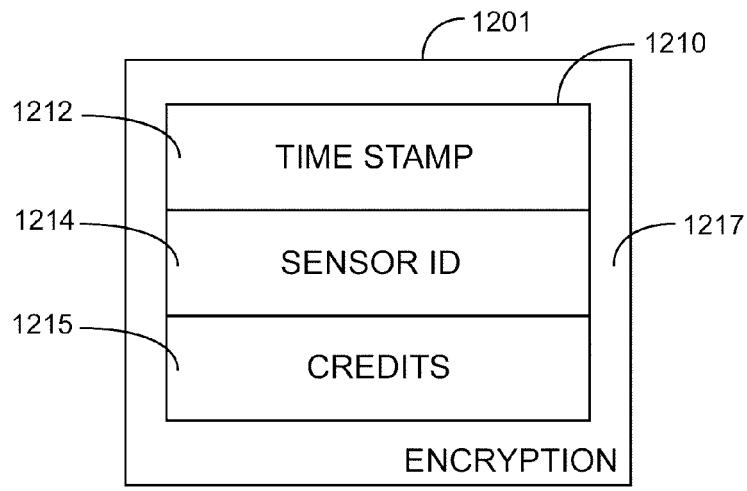
FIGS. 12A-B are a conceptual view of a credit file and a state diagram of a credit file download to a spot check monitor.

FIG. 12A illustrates a credit file 1201 having a time stamp 1212, a sensor ID 1214 and credits 1215. The time stamp 1212 is an integrity feature of the credit file 1201. The sensor stores the time stamp of the last credit file downloaded. A monitor reads the sensor time stamp to verify it is older than the time stamp of the credit file to download. If the sensor time stamp is newer than (or the same as) the credit file time stamp, then the credit file is not downloaded. In this manner, reuse of credits is prevented. In an embodiment, the time stamp 1212 is a universal time code (UTC). In other embodiments, any sequential number scheme can be used in lieu of a time stamp so as to distinguish new and used credit files. In alternative embodiments, verification of a credit file time stamp is done in the sensor or both the sensor and the monitor.

Also shown in FIG. 12A, the sensor ID 1214 is another integrity feature of the credit file 1210. In an embodiment, the sensor ID 1214 is a unique 16 digit (hexadecimal) number assigned to and stored within each spot check sensor 10. A monitor reads the sensor ID to verify it is identical to the credit file sensor ID. If not, the credit file is not downloaded. In this manner, credits purchased by a particular customer for a particular sensor cannot be used by another customer or for another sensor. Advantageously, the time stamp and sensor ID integrity features dissuade the use of counterfeit, knockoff or grey market sensors and facilitate data collection and research, as described with respect to FIG. 4, above.

Further shown in FIG. 12A, the credit file 1201 has a specified number of spot check credits 1215, which can be added to existing sensor credits, if any, so as to replenish sensor usage. In addition, the entire credit file 1201 including the time stamp, ID and credits is encrypted 1217 to further ensure file integrity.

Figure 12B:
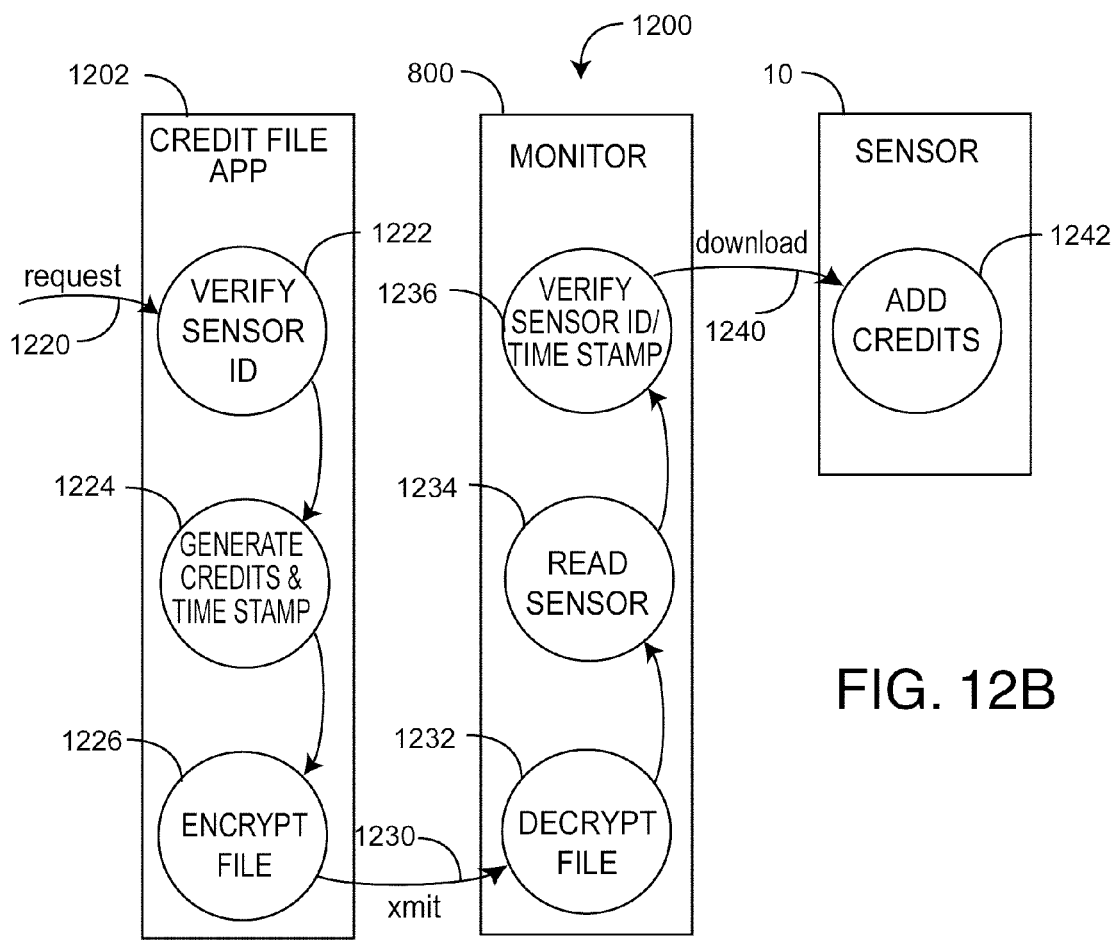

FIG. 12B illustrates a credit file downloading process 1200, which results in credits added to a sensor 10. The process is initiated by a credit request 1220 that is initiated in the web server 1010 (FIG. 10) and relayed to the database server 1030 (FIG. 10) in response to a user or sales request, as described with respect to FIG. 11, above. The database server 1030 (FIG. 10) initiates a spot check credit application 1202 in response, which assembles the credit (binary) file 1201 (FIG. 12A). In particular, a sensor ID validation script 1037 (FIG. 10) verifies the sensor ID 1222 associated with the request. This insures that the addition of sensor credits does not fail when the monitor 800 eventually compares the sensor ID with the ID read from the sensor 10.

As shown in FIG. 12B, the credit file 1201 (FIG. 12A) is then assembled 1224 by generating the time stamp and credits and appending the sensor ID. A script then encrypts the credit file 1226. The web server 1010 (FIG. 10) and intervening computer 1020 (FIG. 10) then transmit 1230 the sensor file to the monitor 800, as described with respect to FIG. 10, above. The monitor 800 decrypts the credit file 1232, reads the sensor 1234 and verifies the sensor ID and time stamp 1236, as described with respect to FIG. 12A, above. Once the credit file is verified, the credits are added 1242 to the sensor 10 in the amount of the credit file credits 1215 (FIG. 12A).

Figure 13A:
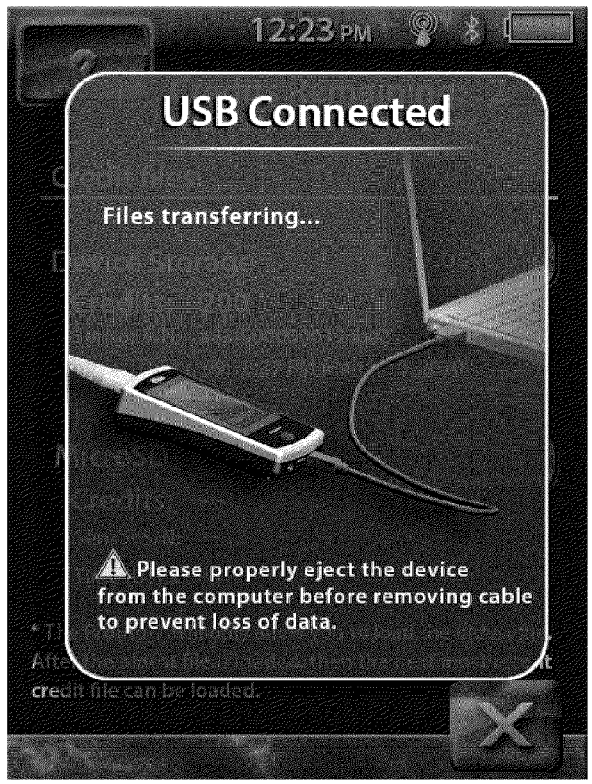
FIGS. 13A-B are spot check monitor screen shots illustrating a sensor credit download via USB cable.
Figure 13B:

FIGS. 13A-B illustrates the downloading of credits via USB cable. New sensors 10 (FIG. 7) typically come with a certain number of credits preinstalled. Each sensor has a serial number that can be found by connecting the sensor to the monitor 800 (FIG. 7) and then selecting Menu>Help>Equipment Report. Once credits are ordered, a digital file is downloaded to a user computer, sent via email or physically mailed on a MicroSD card. Credits are installed onto the sensor via the monitor, as described above, using a MicroSD card or using a USB cable. Using a MicroSD card, the sensor is connected to the monitor, the MicroSD card with spot check credits on it is inserted into the MicroSD card slot, and the MicroSD load button is pressed. A dialog will appear confirming the credits have been successfully loaded.

As shown in FIG. 13A, when a USB cable is connected between a computer and the monitor, the monitor indicates "USB connected." On the computer side, the monitor appears as a mass storage device, e.g. like a USB jump drive. The purchased credit file is then dragged into the monitor "drive." The monitor then indicates "Files transferring." Once the file has completed downloading to the monitor drive, the standard computer procedure for ejecting an external mass storage device is used to "eject" the monitor. The USB cable is then disconnected from the monitor and computer.

As shown in FIG. 13B, after the credit file download, the monitor shows the credit file data including the number of credits, the sensor ID and the time stamp (UTC). The monitor also shows the sensor data including credits remaining the sensor ID. The load button is pressed and a dialog appears confirming the credits have been successfully loaded. If multiple Spot Check credit files have been purchased, the credit files must be loaded in sequential order (i.e. credit file purchased Apr. 3, 2010 prior to credit file purchased Apr. 15, 2010. Non-sequential loading of credit files will obsolete any skipped credit files. If credit files are available in different locations (one on the MicroSD and one on the Internal Device Storage) the monitor only allows loading of the oldest file first. After the oldest file is loaded, then the next most recent credit file can be loaded.

Figure 14:
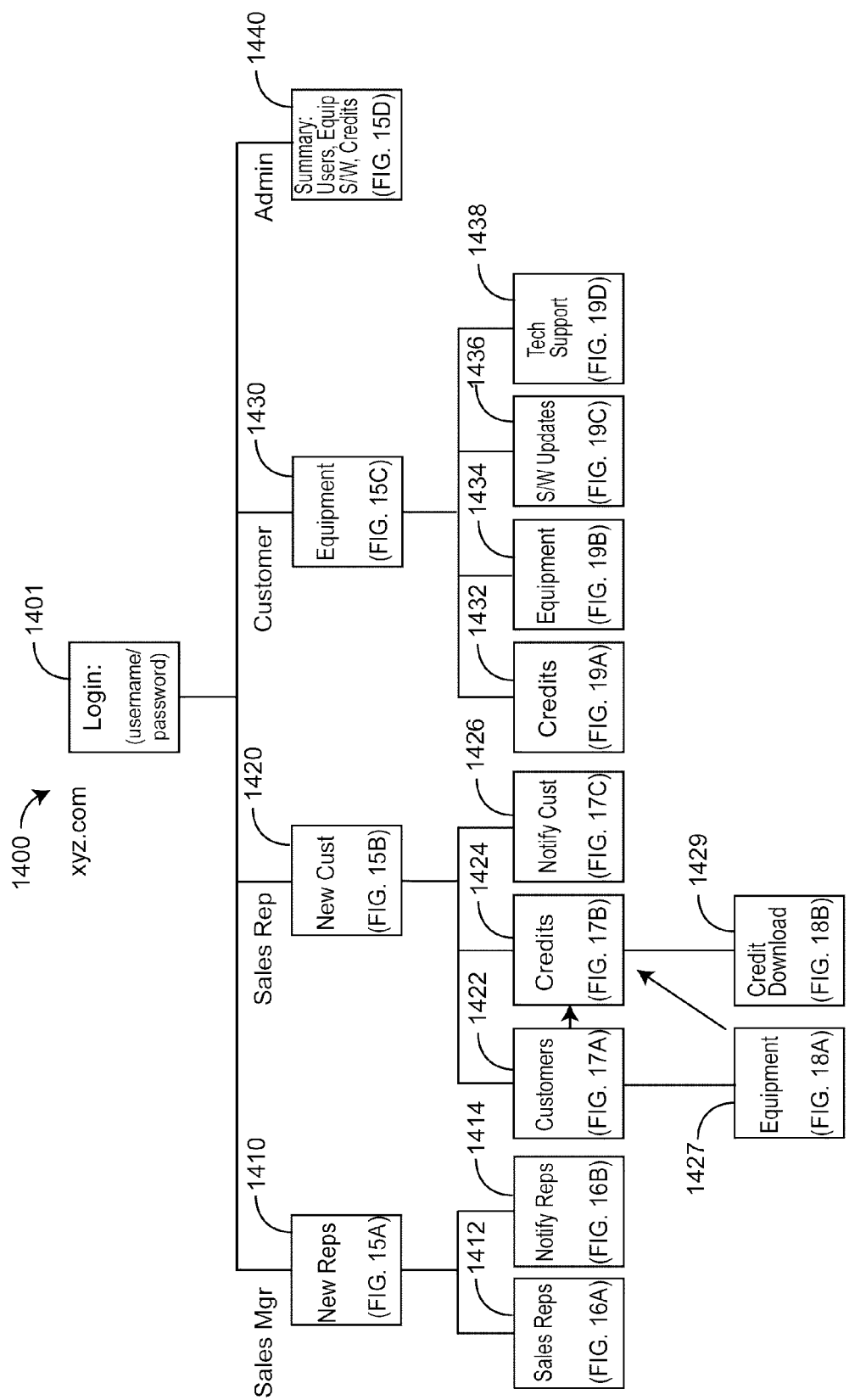
FIG. 14 is a hierarchical page diagram of a spot check credit website.
Figure 15A:
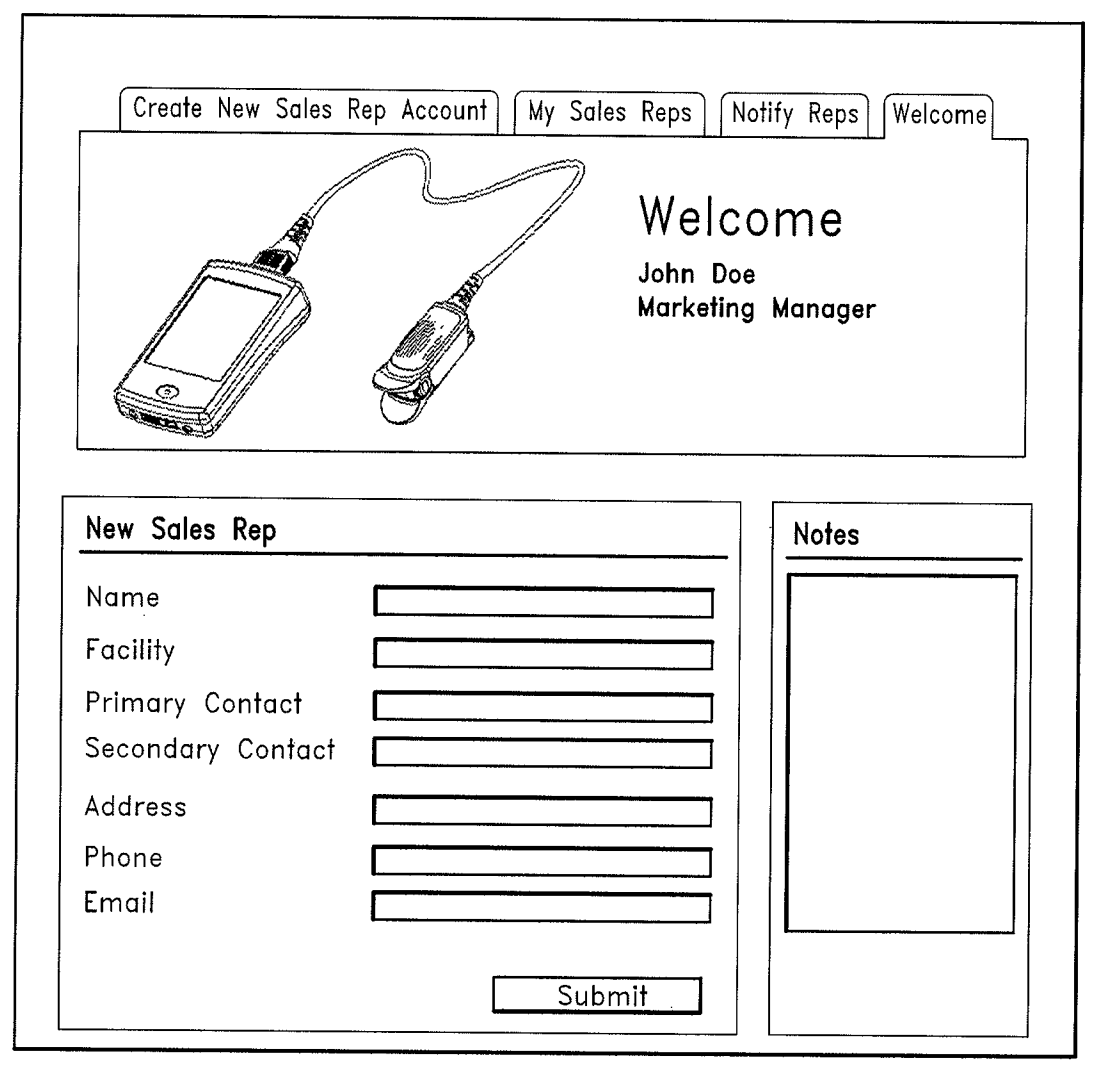
Figure 15B:
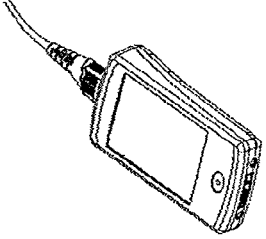
FIG. 15B is a sales representative welcome page.
Figure 15C:
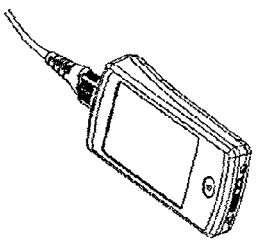
FIG. 15C is a customer welcome page.
Figure 15D:
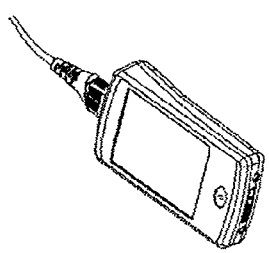
FIG. 15D is an administrator welcome page.

FIG. 14 provides an overview of a spot check credit website having a URL generically described as xyz.com. When a user enters the URL in a browser, the website responds with a login page 1401 requesting a user name and password. When entered, the server recognizes the login as belonging to a sales manager, a sales representative (rep), a customer or a website administrator. If a sales manager logs in, they are directed to a manager's welcome page 1410, as shown in FIG. 15A. If a sales representative logs in, they are directed to a rep's welcome page 1420, as shown in FIG. 15B. If a customer logs in, they are directed to a customer's welcome page 1430, as shown in FIG. 15C. If a site administrator logs in, they are directed to an administrators welcome page 1440, as shown in FIG. 15D.

Figure 16A:
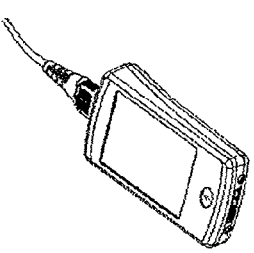
FIGS. 16A-B are sales rep management pages for the sales manager.
Figure 16B:
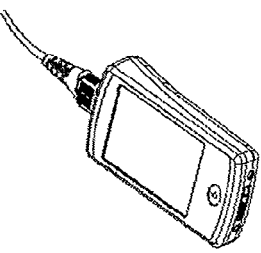
Figure 17A:
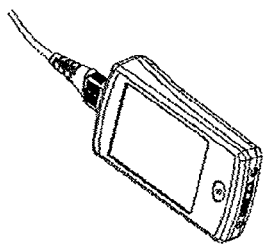
Figure 17C:
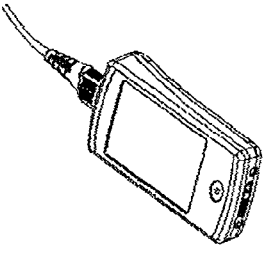
Figure 18A:
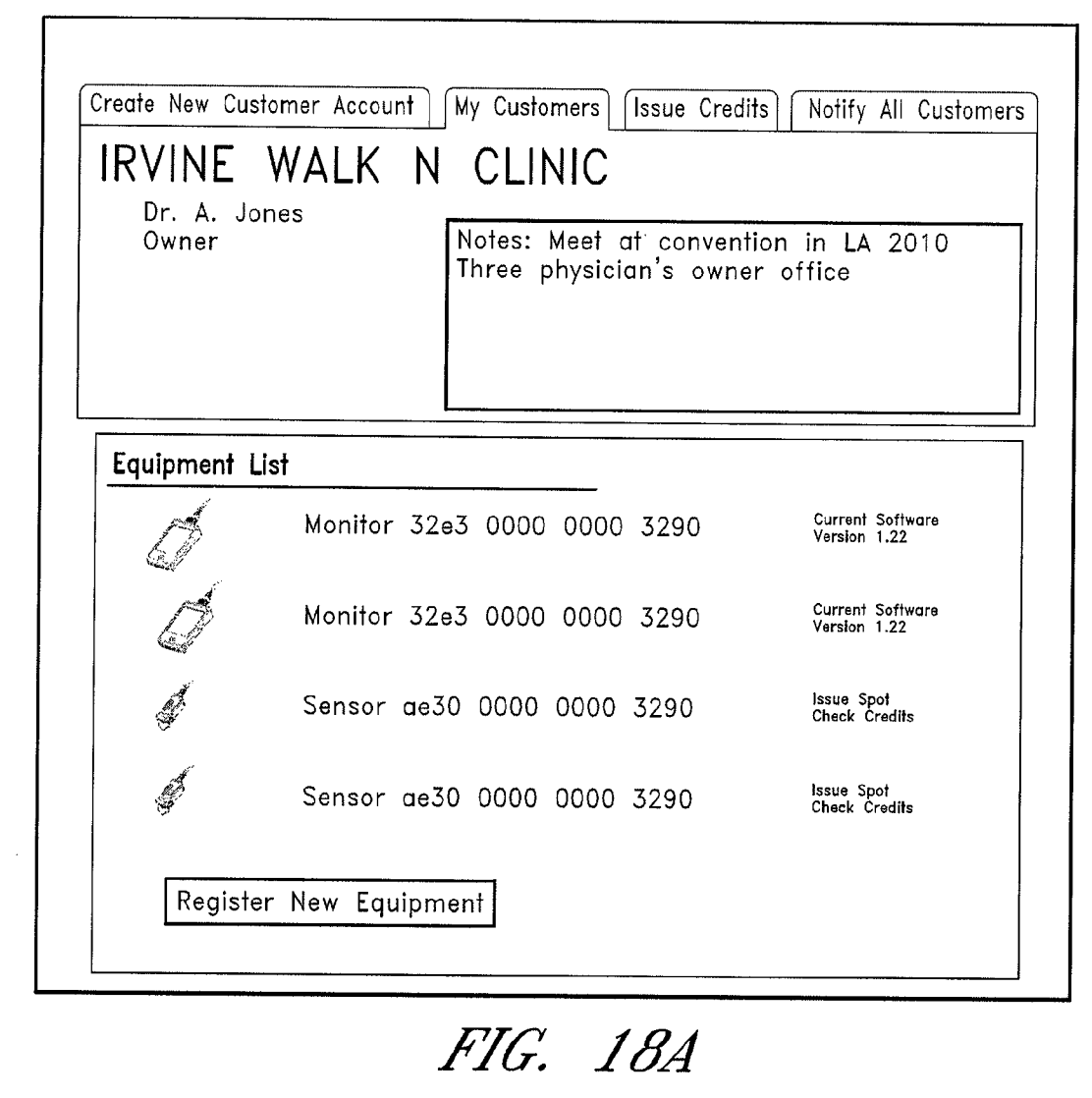
Figure 19B:
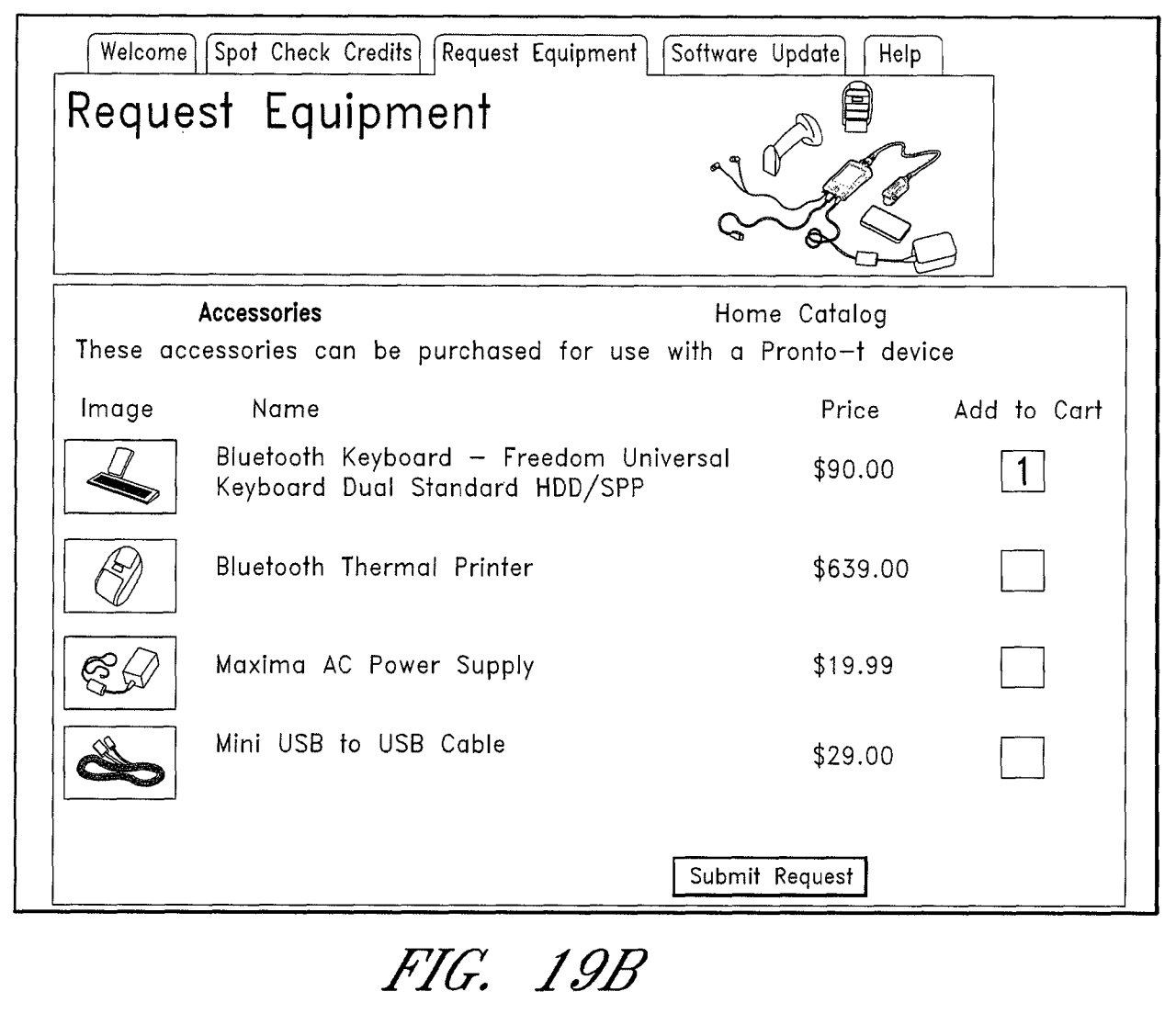
Figure 19C:
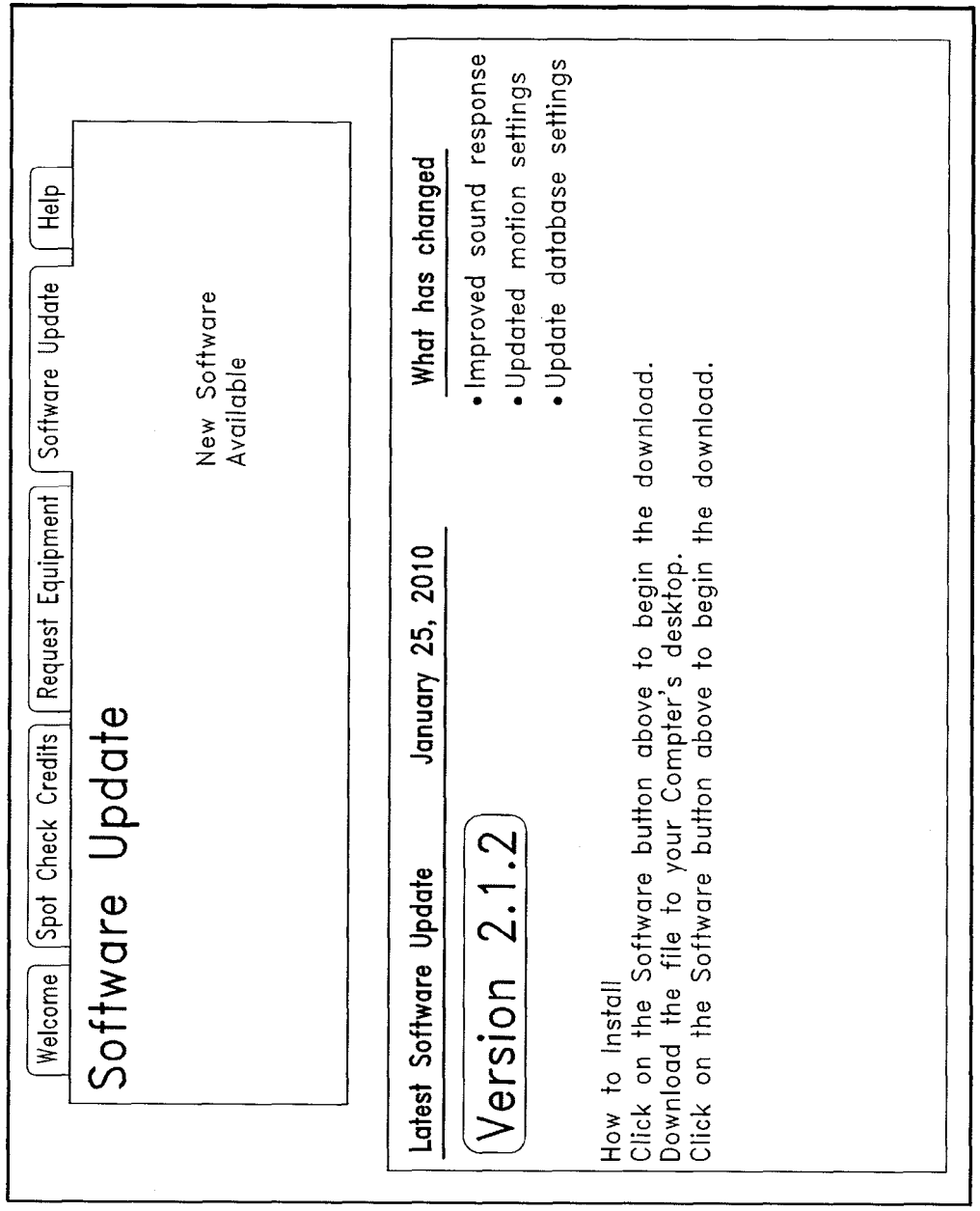
Figure 19D:
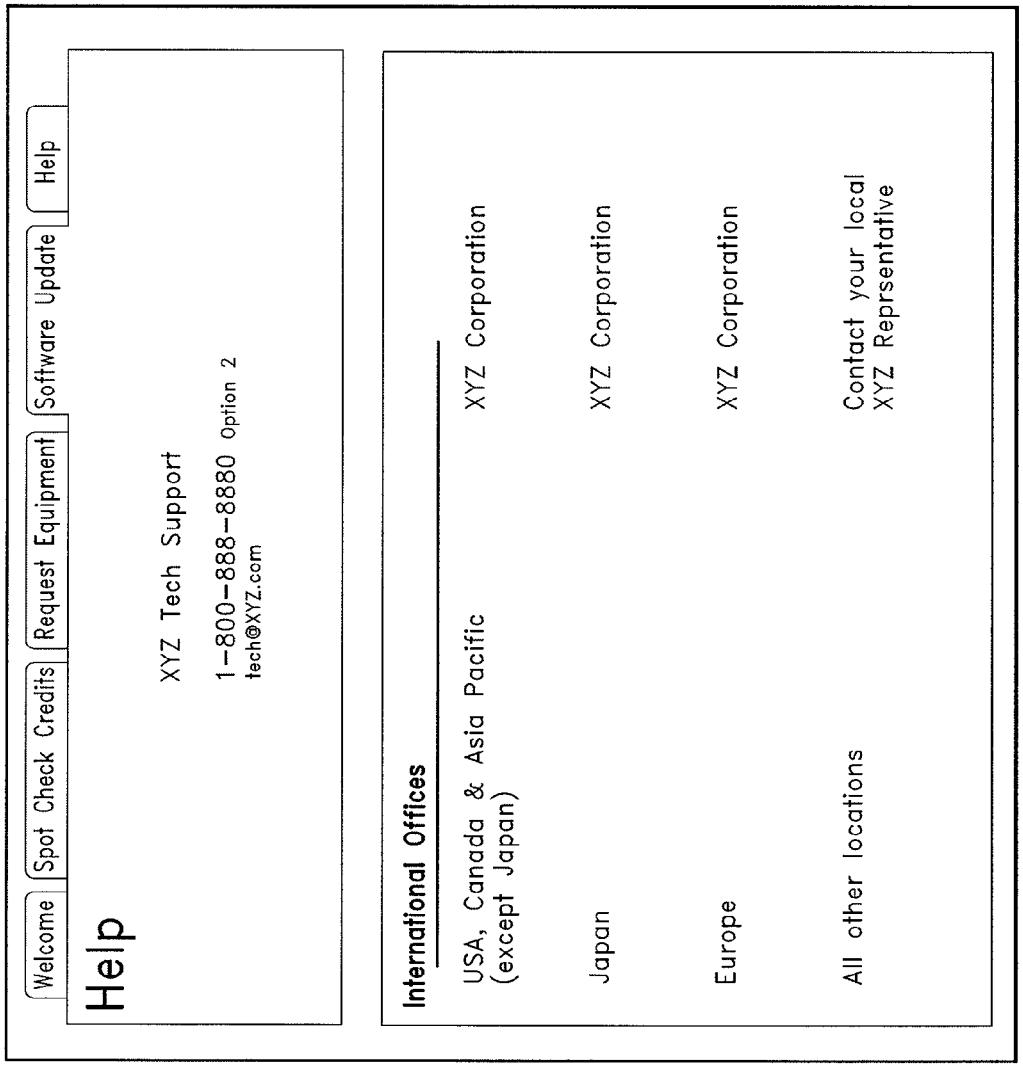

As shown in FIG. 15A, the sales manager's welcome page 1410 has tabs for new reps (default page), my sales reps (FIG. 16A) and notify reps (FIG. 16B). As shown in FIG. 15B, the sales rep's welcome page 1420 has tabs for new customers (default page), my customers (FIG. 17A), issue credits (FIG. 17B) and notify customers (FIG. 17C). Equipment (FIG. 18A) and credit download (FIG. 18B) pages can be accessed via my customers (FIG. 17A) and issue credits (FIG. 17B) pages, respectively. As shown in FIG. 15C, the customer's welcome page 1430 has tabs for equipment (default page), credits (FIG. 19A), request equipment (FIG. 19B), software updates (FIG. 19C) and tech support (FIG. 19D). As shown in FIG. 15D, the administration welcome page 1440 provides a summary of all users, equipment, software updates and credits issued. Additional tabs provide for modifying credit generation script or for uploading software updates, as examples.

In various additional, optional, or combination embodiments, the disclosure herein includes a patient monitor capable of electronically tracking patient measurements on a per-use basis. Moreover, embodiments of the disclosure include a device for communicating with the patient monitor to provide authorization and accounting for measurements, for example, a device that refills or increases the available number of uses left on the patient monitor. In an embodiment, the device includes a photocommunicative key for communicating payment, credit, or other information to the patient monitor to facilitate billing on, for example, a per-use basis. Additionally, the key may advantageously store information, some of which may be sensitive. In an embodiment, the key may include measurement information useful to a manufacturer to manage and improve monitor performance. The key may include measurement information useful to a caregiver, or information useful to a patient being monitored, combinations of the same or the like. This information may include past measurements, trending information, timing of measurements, other parameter information during measurements including vital signs, etc., demographic data, personal medical histories, combinations of the same or the like.

In some embodiments, the photocommunicative key communicates with one or more monitors configured to at least measure a blood analyte through analysis of signals indicative of an absorption of light by tissue. Thus, the monitor is often associated with and designed to provide communication to and from one or more noninvasive sensors, each including a light source or emitter(s) and light detector. The detector is configured to output a signal indicative of light from the light source after attenuation by body tissue. In an embodiment, the key of the present disclosure advantageously communicates with the monitor through the electronics of the noninvasive sensor.

For example, in an embodiment, the key may be configured to communicate through associated pairs of emitters and detectors. For example, the key itself may include one or more detectors capable of outputting a signal responsive to detected light from, for example, the light source(s) of the noninvasive sensor of the monitor. The signals may advantageously be preprocessed and/or forwarded to a key processor or controller configured to determine the information encoded in the detected light. The key processor may also output signals to one or more key light sources or emitters that encode information in a signal of emitted light to be detected by the detector of the noninvasive sensor of the monitor. Through these receiving, decoding, encoding and emitting protocols, the key may advantageously communicate with a patient monitor through, for example, an associated sensor.

Through the foregoing communication, the key may obtain usage information for one or more monitors, manage debits and credits from a credit supply, may obtain software upgrades, firmware for the key and/or the monitor, monitor statistics, monitor and/or supply identifying information, encryption keys, sensor use and/or sensor information, stored monitoring data, combinations of the same or the like. The key may also forward information to one or more patient monitors, the information including some or all of the information received.

In some embodiments, a key encoder may advantageously provide the key with forwardable measurement credits, which the key in turn provides to monitors with whom it communicates. The key encoder may comprise a similar light exchange described above with a sensor or other device specifically designed to communicate with the key, may communicate wirelessly with any multitude of digital processing devices including PCs, phones, servers, and other computing devices, or the like.

In some embodiments, the emitters on the patient monitoring device may be used to provide some or all of the desired power to the photocommunicative key.

For purposes of summarizing the invention, certain aspects, advantages and novel features of the invention have been described herein. Of course, it is to be understood that not necessarily all such aspects, advantages or features will be embodied in any particular embodiment of the invention.

In an embodiment, the present disclosure includes a key or a processing device designed to communicate with a patient monitor. While the communication may include any useful communication between (a) monitors in the field and (b) keys that may be at times communicate with that monitor's manufacturing company, the photocommunicative key of the present disclosure also includes the software and/or hardware providing communication that tracks and accounts for patient use of one or more monitoring devices. For example, in a straightforward implementation, a patient monitor may advantageously track its use through one or more values or formulas. For example, in an embodiment where the monitor provides spot check patient monitoring, such as, for example, total hemoglobin, glucose, ph, oxygen content, other blood analyte, respiration, combination of the same or the like, the monitor may track the number of times it has been used to provide spot check measurements. The monitor may also associate measurements with patient information or codes usable to associate particular measurements, or counts of measurements with a payor of a measured patient's or group of patients' medical care.

It will be appreciated from the disclosure herein that a measurement as disclosed above may have a number of definitions, some preferably associated with a particular monitor's use characteristics or a particular type of billing. For example, in the spot check device of the foregoing, the spot check device may make many actual calculations and take many measurements of one or many physiological parameters, groups or combinations of physiological parameters or the like to determine a single output to the spot check display. In such a device, an embodiment of the disclosure may advantageously use the act of providing a single output to the spot check display as a billable measurement. Alternatively, a user or caregiver input or inputs may identify an activity that qualifies or does not qualify as a billable measurement. For example, a user or caregiver or service representative may delete otherwise billable measurements determined to have been performed unsatisfactorily, in error, as a test or demonstration, as training, as complementary or the like. The billable measurement may be user configurable to adjust to the particular monitoring requirements of a given monitoring situation. In an embodiment, a formula or formulas may be implemented to track what constitutes billable activity on the instrument. For example, a number of electronic events may be included as part of a count or timer where a predetermined total or elapsed time creates a billable event, or the like. In an embodiment, some or all of the formulas may be uploaded from the disclosed key providing adjustable or customizable billing.

In some embodiments, the key may advantageously be a way of tracking multiple billing events and/or entities in a caregiver or other environment. For example, a key may advantageously be provided to each patient at a hospital, caregiver facility or the like. The key may advantageously store all kinds of medically relevant and demographic information about the patient, including for example, recent measurement data from a wide variety of medical monitoring or measurement equipment, caregiver comments, observations, diagnosis, portions or entire medical histories, or the like. An artisan will recognize from the disclosure herein that storage of such data on individual portable memories, such as the foregoing key, reduces the likelihood of privacy violations often found in large monolithic hospital systems.

An artisan will recognize from the disclosure herein a large variety of different accounting methodologies that may be implemented within the monitor to assign billable events to that monitor's activities. For example, in continuous monitoring situations, timers or other use tracking methodologies may be more advantageous that the more straightforward spot check monitor.

In an embodiment the key or digital device may advantageously communicate with the monitor through an attached or communicating sensor. For example, the key may use existing communication protocols between sensors and the monitor to communicate monitor measurement or monitor use information, patient related information, software upgrades, combinations of the same or the like. Such information may include the foregoing accounting type information, may include information useful to the manufacturer to manage monitor behavior and functionality, may include information useful to the patient or caregiver, such as measurement, demographic, patient use or other information, and may include billing information or the like.

Figure 20:
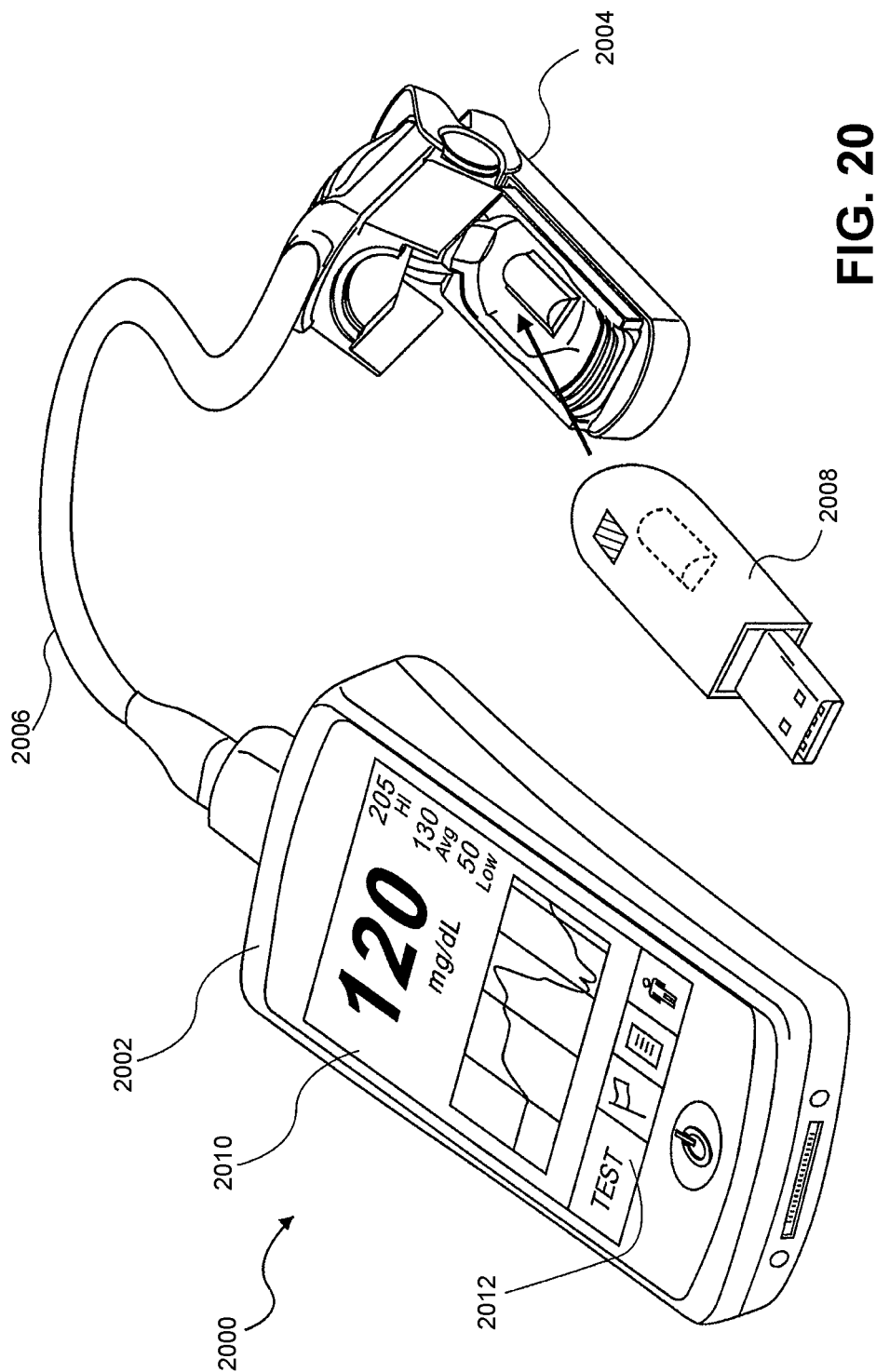
FIG. 20 is an exemplary perspective view of an embodiment of a patient monitor or physiological measurement system including a monitor, a sensor, and a photocommunicative key configured to communicate with the monitor through the sensor.

To facilitate a complete understanding of the invention, the remainder of the detailed description references the figures. For example, FIG. 20 illustrates an exemplary perspective view of an embodiment of a patient monitoring system 2000 including a patient monitor 2002, a sensor 2004, a cable 2006 providing communication between the monitor 2002 and the sensor 2004, and a photocommunicative key 2008 providing communication between the monitor 2002 and the key 2008 through the sensor 2004 and attaching cable 2006. In an embodiment, the patient monitor 2002 comprises a monitoring device configured to process signals indicative of one or more physiological parameters of a patient and determine measurement values for the some, all, or combinations of the parameters. The monitor 2002 outputs those values to the display 2010 or any other connectivity capability built into the monitor 2002 for caregiver review. The monitor 2002 may also include user interaction through user interface devices 2012, which in an embodiment may include control buttons, touchscreens, voice interaction, pointer input, or other common user interface technologies.

Monitors according to the present disclosure can include aspects of those monitors commercially available from Masimo Corporation, Masimo Labs, Inc., or Cercacor Inc., each of Irvine, Calif. In addition, the monitors may comprise monitors disclosed in U.S. Pat. Nos. 6,157,850, 6,584,336, 7,530,949, and U.S. Pat. App. Pub. No. 2010/0030040, owned by Masimo or Cercacor, the content of which at least relating to monitor technologies is incorporated by reference herein.

In an embodiment, the monitor 2002 comprises a spot check monitor for one or more of total hemoglobin, pulse rate, oxygen saturation, carbon monoxide saturation, methemoglobin, brain oxygenation, depth of sedation, glucose, ph, perfusion indications, signal quality indications, combinations of the same or the like. An artisan will recognize from the disclosure herein that other monitors monitoring additional or other parameters may benefit from the accounting disclosure below, and the present disclosure is not limited to the types of specific monitors referenced above.

FIG. 20 also illustrates the sensor 104 comprising a noninvasive reusable sensor including light sources and detectors configured to detect light attenuated by tissue at the measurement site, in this case, at a digit of the patient. Sensors according to the present disclosure can include aspects of those sensors commercially available from Masimo Corporation or Cercacor Corporation, may be disposable, reusable, wireless or combinations of the same. In addition, the sensor may comprise sensors disclosed in U.S. Pat. Nos. 6,088,607, 6,011,986, and U.S. Pat. App. Pub. No. 2010/0030040, owned by Masimo or Cercacor, the content of which at least relating to sensor technologies is incorporated by reference herein.

Figure 22:
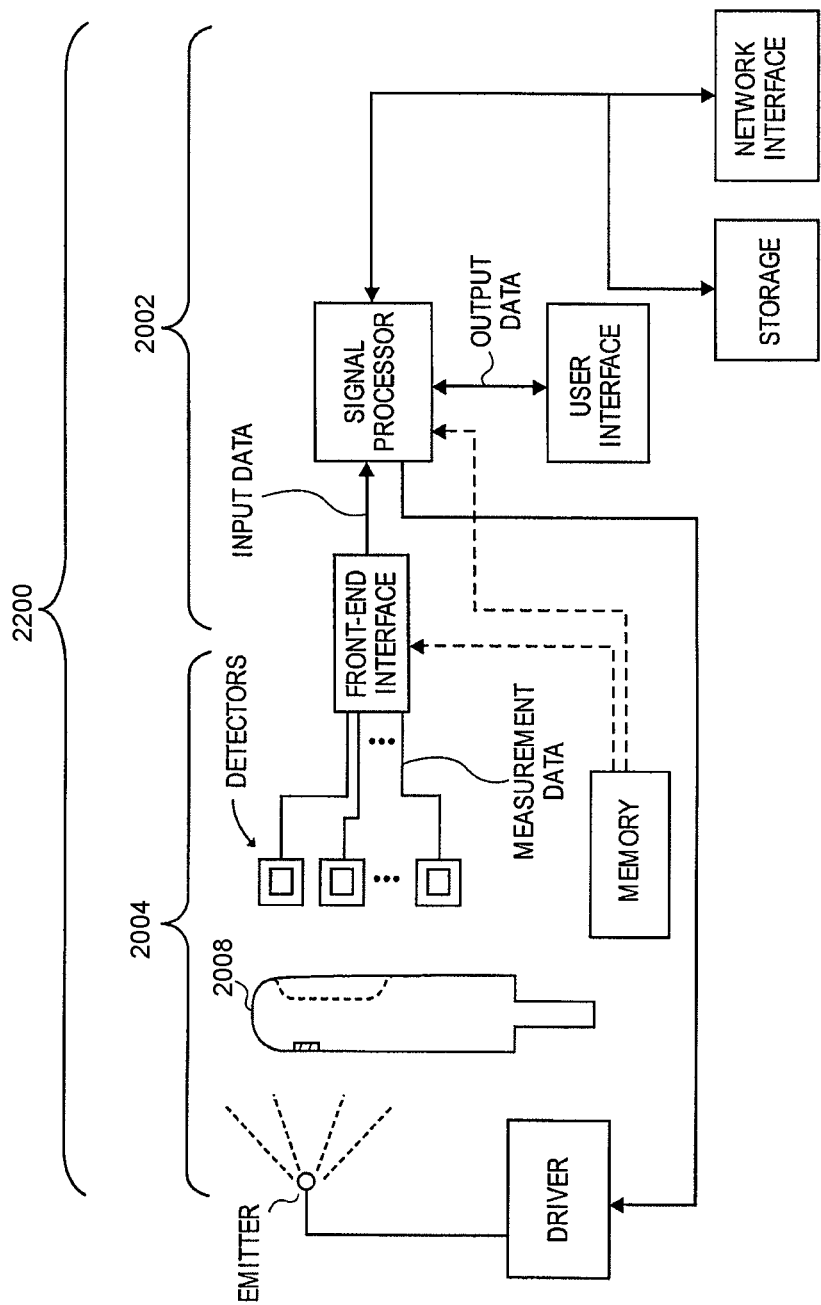
FIG. 22 is an exemplary block diagram of an embodiment of the patient monitor, sensor, and key of FIG. 20.

As is understood in the art and disclosed generally with reference to FIG. 22, the monitor 2002 outputs a drive signal through the cable 2006 to drivers of the light source(s) or emitter of the sensor 2004, causing the light source(s) to emit light. Detectors positioned to receive the emitted light after attenuation by body tissue detect the light and output a signal indicative of the various physiological parameters of the body tissue from the wearer of the sensor 2004. The signal is preprocessed by front end hardware and or software electronics and then forwarded to one or more controllers and/or processors to electronically process the signal and to determine output values for display and eventually caregiver review. In an embodiment, the monitor 2002 includes the display 2010 and the user interface 2012. As shown in FIG. 22, the processor may communicate with memories associated with the sensor, scratchpad memories, software storage, program storage, and the like. In addition, the monitor 2002 may communicate with network interfaces to provide communicate to and from the signal processor.

Returning to FIG. 20, FIG. 20 also shows an embodiment where the key 2008 is shaped to at least roughly mate with mechanical aspects of the sensor 2004 in the sense that coupling of the roughly mateble portions position the key 2008 in a way to ensure optical and/or electronic communication between the key 2008 and the sensor 2004. For example, the key 2008 may include mechanical indentations configured to at least partially match protrusions of the sensor 2004. In an embodiment, the key includes one or more light sources, one or more detectors, and optionally a grip portion and/or a lanyard.

In an embodiment, the monitor 2002 tracks use or is configured to make measurements when there are sufficient measurement credits available. For safety, a certain number of emergency measurements may be implemented to allow measurements without credits. Such measurements may be billed at a later time, possibly with a differing rate, or otherwise be outside the normal spot check per measurement billing methodology. However, in the normal course, when the hand-held monitor 2002 is used, the number of credits available may be decremented. Once there are no credits left, the hand-held device may generally disable itself until more credits are made available. One manner of providing more credits to the hand-held device may be to connect the hand-held device directly to a digital device, possibly via the internet, that can load more credits onto the device. Wireless or other traditional digital device communication, such as through a portable memory, could also be employed. In an embodiment, the key 2008 may include commonly understood communication mechanisms, such as, for example, USB, Bluetooth, or other wireless protocols. As shown, the key 2008 includes optical communication functionality and USB functionality such that the key 2008 may communicate with an instrument or a refill module through optical interactions described further below, and/or through USB communication with PCs, mobile phones, PDAs or other computing devices.

Another manner of getting more credits onto the hand-held device may be to provide the photocommunicative key 2008 that has stored on it credits to be communicated to the monitor 2002. The key 2008 may also be used to provide software or firmware upgrades to the monitor 2002. The key 2008 may communicate with the patient monitor 2002 using a number of different communication components. For example, the patient monitor 2002 may communicate with the key 2008 using photodetectors and photoemitters associated respectively with opposing photoemitters and photodetectors, respectively, of the key 2008. There are several varieties of photosensors and opposing, complementary, matched, or the like, photoemitters that may used for this communication. For example, the photodetectors and photoemitters may advantageously include optical detectors, chemical detectors, such as photographic plates, photoresistors or light dependent resistors (LDR) which may change resistance according to light intensity, photovoltaic cells or solar cells which produce a voltage and supply an electric current when illuminated, photodiodes which may operate in either a photovoltaic mode or a photoconductive mode, photomultiplier tubes, which may contain a photocathode which may emit electrons when illuminated, phototubes, which may contain a photocathode that emits electrons when illuminated, phototransistors, pyroelectric detectors, Golay cells, thermocouples and thermistors, cryogenic detectors, charge-coupled devices (CCD), and/or LEDs reverse-biased to act as photodiodes. The emitters or light sources may be LEDs, halogens, tungsten-based, xenon-based, deuterium-based, or any other type of light source. The words "emitter" and "detector" as used herein may correspond to any or multiple of the types of photodetectors or photoemitters, or groups of detectors or emitters, disclosed, referenced, or implied herein or in the art.

Figure 21A:
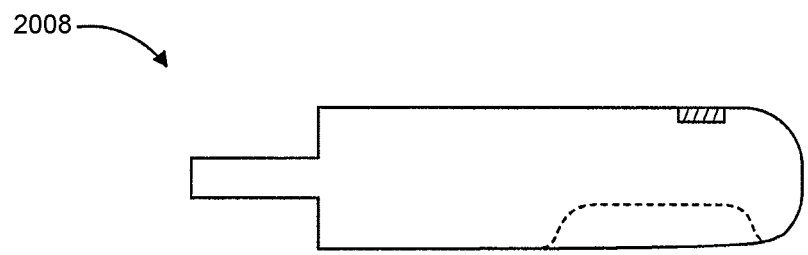
FIGS. 21A-D are simplified side, elevation, bottom, and perspective exemplary views of embodiments of the key of FIG. 20.
Figure 21B:
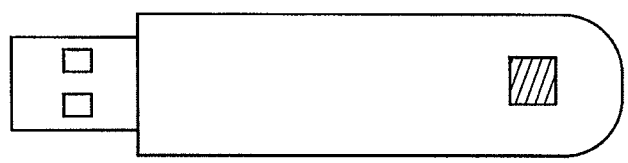
Figure 21C:
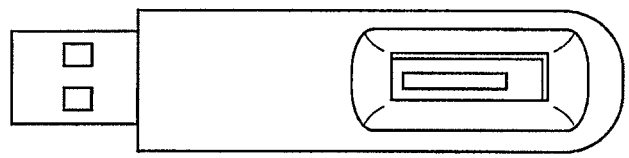
Figure 21D:
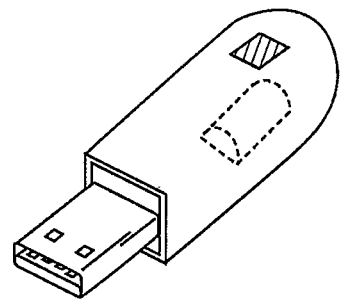

As shown in FIGS. 21A-21D, the photocommunicative key 2008 may at least in part be roughly be shaped like a finger, or substantially cylindrical, to allow it to at least partially mechanical mate with the structure of a given sensor 2004 such that the optical elements are correctly and straightforwardly aligned when the key 2008 is inserted into the sensor 2004. As shown in FIGS. 20-21, in an exemplary embodiment, the sensor 2004 may include a raised ridge within the fingerbed to, for example, create a more consistent and predictable finger shape when the sensor 2004 is taking measurements. As shown in FIG. 21C, the shape of the raised ridge may be advantageously hollowed out of the shape of the key 2008 to ensure proper vertical and horizontal alignment when the key is inserted into the sensor 2004. Additionally, transparent windows may advantageously cover and protect at least the emitter and detector light paths of the key 2008 allowing light to pass through portions thereof. In an embodiment, the internals of the key 2008 may be advantageously formed, coated, or otherwise configured to reduce light received from the emitters of the sensor 2004 from bleeding or piping through the key 2008 to the detectors of the sensor 2004.

FIG. 21 also shows that the key may include a grip portion for straightforward handling. An artisan will recognize from the disclosure herein that the shape of the key 2008 can take many forms. Considerations in shaping the key may include mechanical stops or gaps that mate or substantially mate with the sensor 2004 or other mating device to properly position the key for communication, such as, for example, optical communication through transparent windows. The key 2008 may be shaped to reduce light piping or interference from exterior light or noise sources. The key 2008 may be shaped, colored, and/or branded to uniquely identify its manufacturer, controller, service provider or the like. If the patient monitor 2002 or sensor 2004 is configured or shaped to monitor another body part, such as an ear lobe, then the photocommunicative key may be shaped to match that body part. If the patient monitor 2002 has particularly-shaped padding, the key 2008 may be shaped to fit well in only one manner with the padding on the patient monitor 2002. In an embodiment, the key 2008 may use any appropriate voltage and amperage, corresponding to any communication or other scheme, protocol, or the like, such as, for example, approximately 5 volts at approximately 30 milliamperes; however many other combinations are within the scope of the disclosure.

In an embodiment, a digital processor may program the key 2008 to, for example, communicate payment or credit information. In an embodiment, a processor communicates with a communication module that may advantageously include lights sources and detectors similar to that described below with reference to key-sensor communication. That is, an emitter may emit radiation detectable by the key detector and the signal may be translated into an electronic signal and sent to the key processor to update, for example, measurement credits available on the key 2008 or subscription information or, in some embodiments, upgrade to software or firmware.

In some embodiments, the instrument may receive credit information or subscription information via the Internet or a direct connection between the instrument and a device capable of providing credit information or subscription information, such as a personal computer, cell phone, or the like.

In some embodiments, some or all of the communication disclosure herein may be encrypted. Those of ordinary skill in the art will be familiar with the encryption techniques useful for encrypting the stored data and communications, including public/private key encryption, password-based encryption, secret-key-based encryption, or the like. Encryption may be used to make copying or duplicating the information on the photocommunicative key 2008 or the patient monitor 2002 difficult. Encryption may also alleviate some potential privacy concerns with the storage and transmittal of usage information.

FIG. 22 illustrates an exemplary block diagram of the key 2008 in communication with a patient monitor 2002 through the sensor 2004. In some embodiments, the key 2008 may include one or more detectors, one or more emitters, one or more memories, or the like each communicating with one or more microprocessors or controllers. In addition, the key 2008 may include preprocessing modules for noise reduction. As will be understood from the disclosure herein, electronic components of the key 2008 may communicate with one another along conductive paths as part of a printed circuit board, as separate components, across wires, or the like. For example, the microprocessor may be coupled to detectors as well as to memory and the emitters. As is discussed in more detail herein, the key memory may store information relating to credits, subscriptions, patient information, measurement or operational information, and/or software or firmware upgrades for patient monitor 2002.

The key microprocessor may be used to generate a signal to be sent out by the emitter based on information stored in the key memory. For example, if the key memory is storing information relating to additional credits, then the key microprocessor may generate a signal to be emitted by emitter and detected by patient monitor's detector and therefrom communicated to instrument. The same general process may be used to communicate subscription information or software or firmware upgrades from the key 2008 to patient monitor 2002. Once successfully communicated, credit or subscription information stored on memory may be deleted or otherwise invalidated so that it may not be used again. Reverse path communication is also envisioned, for example, where the emitters of the monitor 2004 communicate signals representing patient information, monitor information, use information, patient data, clinical data, alarm data, or the like to the key 2008 for later uploading to other devices for manufacturer or other review and analysis.

In some embodiments, the key microprocessor may also be another form of computing device such as a central processing unit, graphics processing unit, application-specific integrated circuit, other dedicated hardware or programmed general purpose hardware, or any other device capable of handling the functions of a microprocessor or controller. The key memory may include a random-access memory (RAM), a read-only memory (ROM), a programmable read-only memory (PROM), and an erasable PROM (EPROM), a Flash-EPROM, or any other memory chip or cartridge. In some embodiments, the memory may include a computer-readable media, such as a floppy disk, a flexible disk, hard disk, magnetic tape, or any other magnetic media, a CD-ROM, DVD, any other optical media, punch cards, paper tape, any other physical media with patterns of holes.

In some embodiments, an additional detector may be used to receive photoenergy from emitters of the sensor 2004 or any key programming device, thereby providing power to the key 2008. For example, if a sensor 2004 comprises a plurality of LEDs, such as, for example, four, eight, sixteen, or the like, and a plurality are activated in a manner than efficiently powers the key 2008. For example, duty cycles may advantageously be varied when powering the key as opposed to simple communication. Powering photocommunicative key 2008 in this way may extend its shelf life and may eliminate the need to provide new batteries. Alternatively, artisans will recognize from the disclosure herein a myriad of powering technologies usable for the key 2008.

Information regarding debits, credits, subscription information, patient information such as test results, measurement or demographic data or the like, or upgrades may be communicated to photocommunicative key 2008 in a manner similar to that described with respect to FIG. 21 for communication of information between patient monitor 2002 and photocommunicative key 2008. For example, a refill module may communicate debit, credit, subscription, patient, monitor or upgrade information. The refill module may also store usage information for later billing to be performed based on the usage information stored on photocommunicative key 2008. In some embodiments, billing information may also be sent from photocommunicative key 2008 to an information module via wired or wireless interface, USB, or other communication protocol recognizable to an artisan as appropriate for the disclosure herein.

Figure 23:
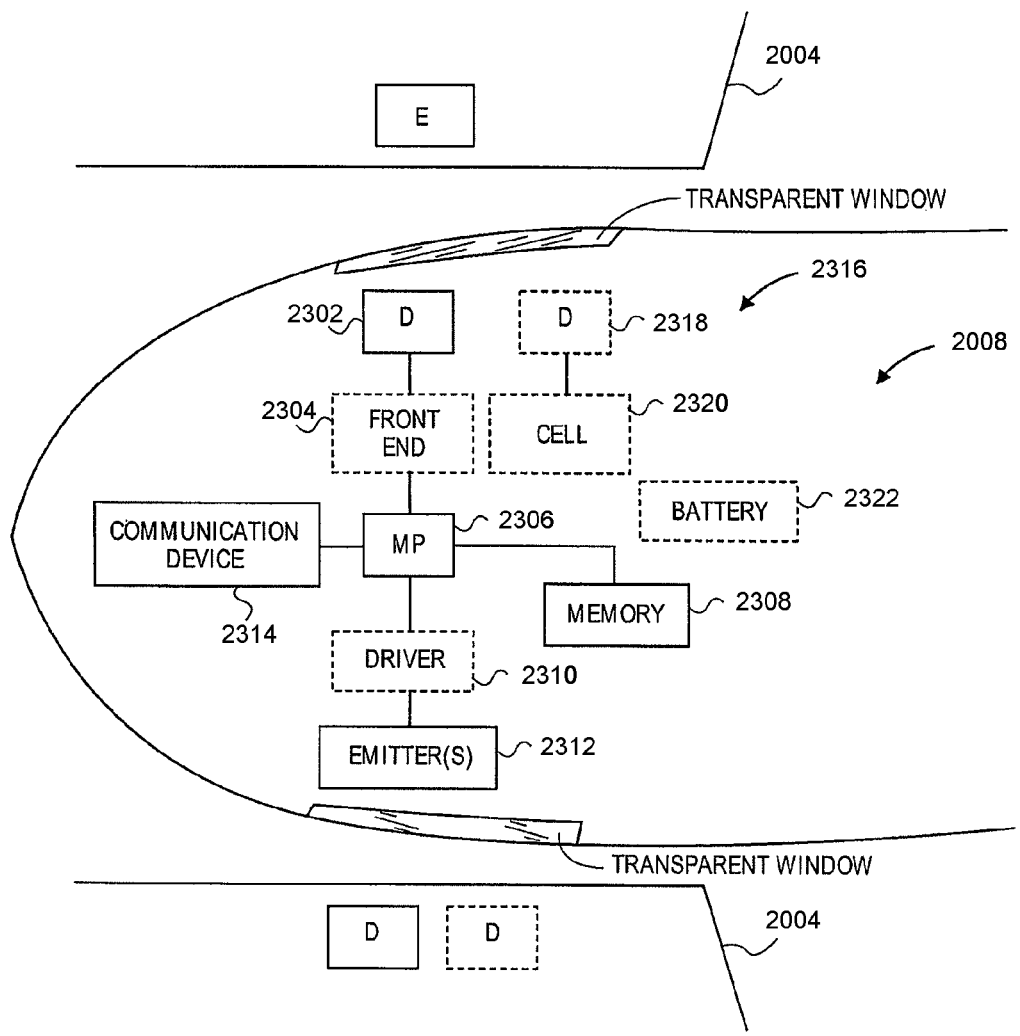
FIG. 23 is an exemplary block diagram of the key of FIG. 20.

FIG. 23 illustrates an exemplary block diagram of the key 2008 of FIG. 20. As shown in the embodiment of FIG. 23, the key 2008 includes one or more photodiodes 2302 receiving optical signals from, for example, the emitter of the sensor 2004. These optical signals may be optionally preprocessed with appropriate analog and/or digital circuitry 2304 to remove noise and/or boost gain and then forwarded to a microprocessor 2306. To communicate back to an instrument, the microprocessor 2306 may optionally output signals to digital and/or analog circuitry 2310 configured to drive one or more emitters 2312 that optically communicate with, for example, the detectors of the sensor 2004. The microprocessor 2306 may also advantageously communicate with a memory 2308 and a communication device 2314. The communication device 2314 may advantageously comprises appropriate circuitry for USB communication, Bluetooth or other wireless communication, wired communication or the like. As mentioned, the key 2008 may advantageously include transparent windows allowing for the optical transmission of signals. Moreover, the windows may be coated or shaded to reduce unwanted noise and/or interfering wavelengths of light.

In an embodiment, the key 2008 also includes one or more additional detectors 2318 configured to use emitted light to acquire energy to power the key 2008. In such an embodiment, the detectors 2318 communicate with a storage cell 2320 to, for example, store and regulate energy received from the emitters of the sensor 2004. In alternative embodiments, replaceable or other batteries may provide sufficient power to the key 2008. In any event, the key 2008 acquires sufficient power to operate the microprocessor 2306 and at least one of the communication device 2314 and the emitters 2312 to enable communication of data, such as, for example, credit information and other data described herein to a corresponding communication device such as the sensor 2004.

An artisan will understand from the disclosure herein that such communication with the key 2008 may advantageously be between the key 2008 and a monitor 2002, or between the key 2008 and a key programming device, such as, for example, a refill module or the like.

Figure 24:
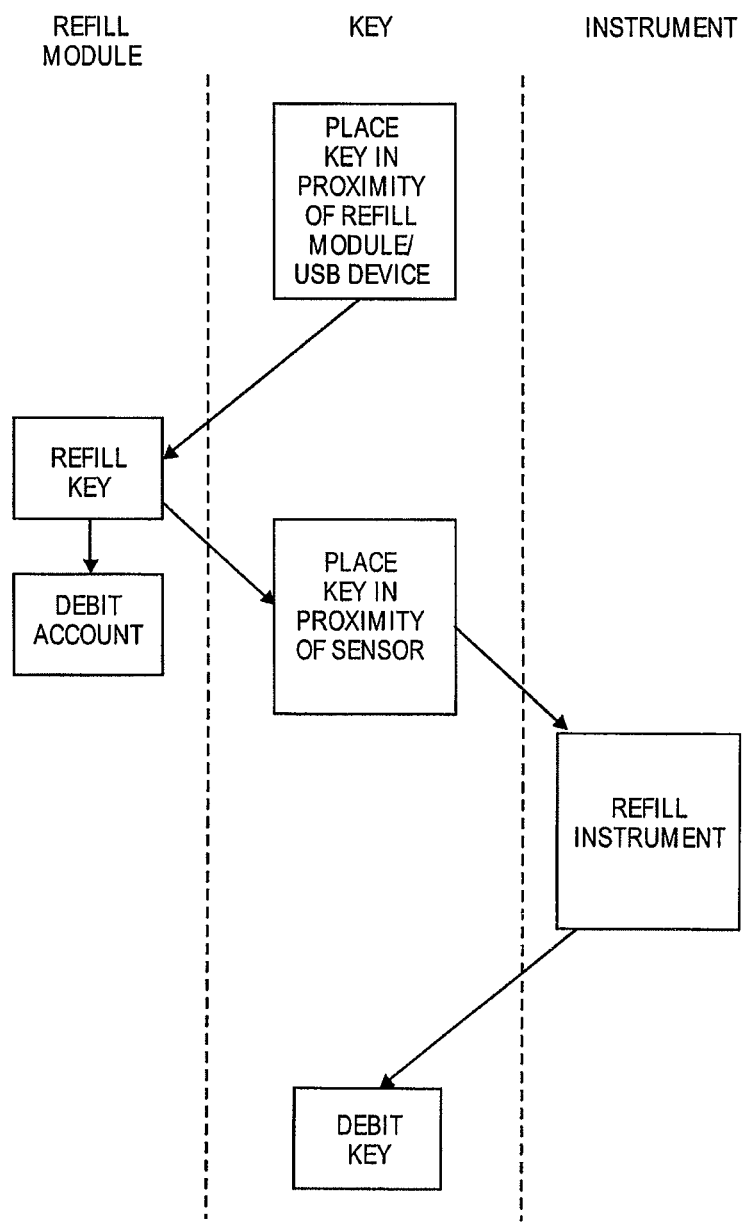
FIG. 24 is a simplified flow chart of a measurement refill process, according to an embodiment of the key of FIG. 20.

FIG. 24 illustrates a simplified flow chart of a measurement refill process, according to an embodiment of the key 2008 of FIG. 20. In an initial step, the key 2008 may be placed within communication proximity of a refill module, whether that is communicating through emitters and detectors, through wired or wireless devices, USB connectivity, or the like will at least in part dictate the specifics of the proximity of the key to the refill device. As shown in FIG. 24, once connection is established with respect to the refill module, the module may refill the key and perform accounting procedures with respect to measurements taken by certain monitors, certain accounts, certain patients, combinations of the same or the like. Once the key 2008 is refilled, the key is placed in proximity of the sensor 2004. As described above, the proximity may advantageously include a portion of mechanical mating elements aligning.

Once communication between the key 2008 and the monitor 2004 is established, the number of spot check measurements may advantageously be increased on the monitor 2004. Additionally, the communication may include a myriad of other one or two way exchanges of information, such as the information described herein above.

Figure 25:
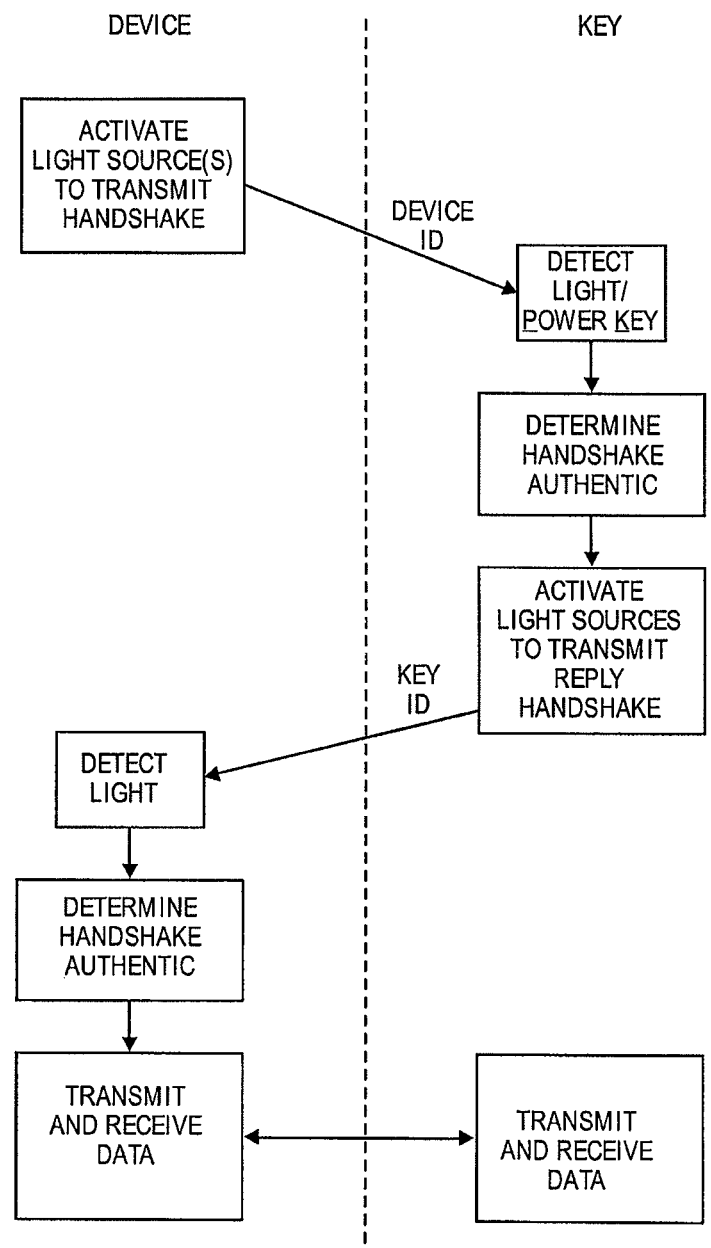
FIG. 25 is a simplified flow chart of a communication process between the key of FIG. 20 and a patient monitor, according to an embodiment of the disclosure.

FIG. 25 illustrates a simplified flow chart of a communication process between the key 2008 of FIG. 20 and a patient monitor 2004, according to an embodiment of the disclosure. For example, the key detectors 2302 may detect light from the emitters of the monitor 2004. The light may be advantageously organized such that some of the light provides communication and some of the light provides power for the electronics of the key 2008, although powering may simply be provided from another power source. The key 2008 may determine whether proper handshaking protocols have been followed and/or encryption secrets properly passed. This handshaking may include multiple back-and-forths between the key 2008 and the monitor 2004. To reply to the monitor 2004, the key light sources 2312 activate in a predetermined manner understood by the monitor 2004 to create a signal encoded with information for the key 2008.

The processes, computer readable media, and systems described herein may be performed on various types of hardware, such as hand-held devices or computer systems. Hand-held devices may include personal data assistants, cell phones, portable music players, laptops, and any other portable computing device. Computer systems and hand-held devices may include a bus or other communication mechanism for communicating information, and a processor coupled with the bus for processing information. A hand-held device or computer system may have a main memory, such as a random access memory or other dynamic storage device, coupled to the bus. The main memory may be used to store instructions and temporary variables. The computer system may also include a read-only memory or other static storage device coupled to the bus for storing static information and instructions. The hand-held device or computer system may also be coupled to a display, such as a CRT or LCD monitor. Input devices may also be coupled to the computer system. These input devices may include a mouse, a trackball, or cursor direction keys. Computer systems or hand-held device described herein may include patient monitor 2002, sensor 2004, or photocommunicative key 2008. Each computer system may be implemented using one or more physical computers or computer systems or portions thereof. The instructions executed by the hand-held device or computer system may also be read in from a computer-readable media. The computer-readable media may be a CD, DVD, optical or magnetic disk, laserdisc, carrier wave, or any other media that is readable by the computer system. In some embodiments, hardwired circuitry may be used in place of or in combination with software instructions executed by the processor.

As will be apparent, the features and attributes of the specific embodiments disclosed above may be combined in different ways to form additional embodiments, all of which fall within the scope of the present disclosure. For example, the monitors of the present disclosure may advantageously track the useful and safe life of an attached sensor or other accessory through a timing or countdown process, perhaps similar to a reverse automobile odometer, as well as separately tracking pay-per-use or per group of use or other currency based monitoring.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable media or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

Although the foregoing invention has been described in terms of certain preferred embodiments, other embodiments will be apparent to those of ordinary skill in the art from the disclosure herein. For example, when the electronic components of a monitor include reusable yet separable electronics such as a Y-type sensor, those electronics may plug into receptacles on a key that could then have virtually any shape, including shapes designed to minimize interfering light or other noise. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

A spot check monitor credit system has been disclosed in detail in connection with various embodiments. These embodiments are disclosed by way of examples only and are not to limit the scope of the claims that follow. One of ordinary skill in art will appreciate many variations and modifications.

What is claimed is:

1. A photocommunicative key for communicating with a patient monitor, the patient monitor in communication with a noninvasive reusable sensor configured to detect light attenuated by patient tissue at a measurement site, the photocommunicative key comprising:
 a body;
 a photodetector positioned within the body;
 a photoemitter positioned within the body;
 a memory module positioned within the body, the memory module configured to store information for communication with the patient monitor; and
 a processor positioned within the body and electrically coupled to the photodetector, the photoemitter, and the memory module, the processor configured to:
 process signals from the photodetector,
 generate signals to be sent to the photoemitter, and
 store information in the memory,
 wherein the body of the photocommunicative key is shaped to mate with mechanical aspects of the noninvasive reusable sensor such that coupling the body to the noninvasive reusable sensor creates an optical communication link between the photoemitter and the noninvasive reusable sensor,
 wherein the processor, in use, generates a signal to be sent to the patient monitor thru the noninvasive reusable sensor and the optical communication link, the signal comprising at least some of the information stored in the memory encoded thereon,
 wherein the photoemitter receives the generated signal from the processor and emits an optical signal to be detected by the noninvasive reusable sensor.

2. The photocommunicative key of claim 1, wherein the body of the photocommunicative key is shaped similar to a finger of a patient.

3. The photocommunicative key of claim 1, wherein the body of the photocommunicative key includes mechanical indentations configured to partially match protrusions of the noninvasive reusable sensor.

4. The photocommunicative key of claim 1, further comprising:
   an electrical connector coupled to the body, the electrical connector configured to mate with a corresponding electrical receptacle in a computing device; and
   an electrical detector electrically coupled to the electrical connector and the processor, the electrical detector configured to receive electrical signals from the computing device through the electrical connector; and
   an electrical emitter electrically coupled to the electrical connector and the processor, the electrical emitter configured to transmit electrical signals to the computing device through the electrical connector.

5. The photocommunicative key of claim 1, wherein the body of the photocommunicative key is substantially cylindrical.

6. The photocommunicative key of claim 1, wherein coupling the body to the noninvasive reusable sensor substantially aligns the photoemitter with a photodetector in the noninvasive reusable sensor such that at least a portion of light emitted by the photoemitter is received by the photodetector in the noninvasive reusable sensor.

7. The photocommunicative key of claim 1, wherein coupling the body to the noninvasive reusable sensor substantially aligns the photodetector to receive at least a portion of a light signal from the noninvasive reusable sensor.

8. The photocommunicative key of claim 1, wherein the body comprises a physical feature that mates with a corresponding physical feature of the noninvasive reusable sensor such that coupling the photocommunicative key to the noninvasive reusable sensor comprises mating the physical feature with the corresponding physical feature.

9. The photocommunicative key of claim 1, wherein the body comprises transparent windows to cover the photoemitter and the photodetector, wherein the transparent windows are configured to allow portions of light to pass between the noninvasive reusable sensor and the photoemitter and the photodetector.

10. The photocommunicative key of claim 9, wherein the transparent windows are coated to reduce selected wavelengths of light from being transmitted through the transparent windows.

11. The photocommunicative key of claim 1, further comprising a storage photodetector configured to receive a second optical signal to acquire electrical energy to provide power to the photocommunicative key.

12. The photocommunicative key of claim 11, wherein the storage photodetector is configured to communicate with a storage cell to store energy acquired from the received second optical signal.

* * * * *